(12) United States Patent
Moriyasu

(10) Patent No.: US 12,094,036 B2
(45) Date of Patent: Sep. 17, 2024

(54) MEDICAL IMAGE PROCESSING APPARATUS, AND NUCLEAR MEDICINE DIAGNOSIS APPARATUS

(71) Applicant: CANON MEDICAL SYSTEMS CORPORATION, Otawara (JP)

(72) Inventor: Kenta Moriyasu, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 462 days.

(21) Appl. No.: 16/931,642

(22) Filed: Jul. 17, 2020

(65) Prior Publication Data
US 2021/0019924 A1 Jan. 21, 2021

(30) Foreign Application Priority Data
Jul. 18, 2019 (JP) ................. 2019-132849

(51) Int. Cl.
G06T 11/00 (2006.01)
A61B 6/03 (2006.01)
A61B 6/04 (2006.01)
G06T 7/00 (2017.01)
G06T 7/70 (2017.01)

(52) U.S. Cl.
CPC ............ G06T 11/005 (2013.01); A61B 6/037 (2013.01); A61B 6/04 (2013.01); G06T 7/0012 (2013.01); G06T 7/70 (2017.01); G06T 2207/10104 (2013.01); G06T 2207/20036 (2013.01); G06T 2207/20081 (2013.01); G06T 2207/30004 (2013.01); G06T 2207/30242 (2013.01)

(58) Field of Classification Search
CPC .................. G06T 11/006; G06T 2207/10104
See application file for complete search history.

(56) References Cited

U.S. PATENT DOCUMENTS

| 8,000,513 | B2* | 8/2011 | Defrise | G06T 11/006 |
| | | | | 382/128 |
| 11,069,098 | B2* | 7/2021 | Dwivedi | A61B 6/037 |
| 2010/0098312 | A1* | 4/2010 | Leahy | G01T 1/2985 |
| | | | | 382/131 |
| 2011/0081068 | A1* | 4/2011 | Brinks | G06T 11/005 |
| | | | | 250/363.03 |

(Continued)

FOREIGN PATENT DOCUMENTS

WO WO-2019183584 A1 * 9/2019 ............. A61B 6/032

OTHER PUBLICATIONS

Disclosed Anonymously, Deep Learning Based Attenuation Correction for Time-of-Flight Position Emission Tomography, IP.com No. IPCOM000249029D, Jan. 27, 2017, p. 1-5 (Year: 2017).*

*Primary Examiner* — Gandhi Thirugnanam
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to obtain Time-of-Flight (TOF) depiction image data generated on the basis of an annihilation point of a gamma ray. The processing circuitry is configured to output reconstructed Positron Emission computed Tomography (PET) image data on the basis of the TOF depiction image data and a trained model that outputs the reconstructed PET image data on the basis of an input of the TOF depiction image data.

11 Claims, 17 Drawing Sheets

(56) References Cited

U.S. PATENT DOCUMENTS

| | | | | |
|---|---|---|---|---|
| 2012/0070057 | A1* | 3/2012 | Zhang | G06T 11/005 |
| | | | | 382/131 |
| 2013/0134311 | A1* | 5/2013 | Takayama | G01T 1/164 |
| | | | | 250/362 |
| 2014/0003689 | A1* | 1/2014 | Asma | G06T 11/006 |
| | | | | 382/131 |
| 2015/0065854 | A1* | 3/2015 | Ahn | A61B 6/5247 |
| | | | | 600/411 |
| 2017/0358087 | A1* | 12/2017 | Armeni | G06K 9/6285 |
| 2018/0144513 | A1* | 5/2018 | Liu | G06T 7/0012 |
| 2018/0353147 | A1* | 12/2018 | Wang | G06T 11/005 |
| 2019/0066341 | A1* | 2/2019 | Feng | G06T 11/003 |
| 2019/0108904 | A1* | 4/2019 | Zhou | G06K 9/6298 |
| 2019/0355159 | A1* | 11/2019 | Bai | H04L 61/5014 |
| 2019/0365341 | A1* | 12/2019 | Chan | A61B 6/5258 |
| 2020/0005495 | A1* | 1/2020 | Teshigawara | G16H 30/40 |
| 2020/0066009 | A1* | 2/2020 | Dwivedi | G06T 11/006 |
| 2021/0019924 | A1* | 1/2021 | Moriyasu | A61B 6/0407 |
| 2023/0089212 | A1* | 3/2023 | Hashimoto | G16H 20/10 |
| | | | | 705/2 |
| 2024/0112379 | A1* | 4/2024 | Zhao | A61B 6/037 |

* cited by examiner

| MODULE ID | SCINTILLATOR NUMBER (P) | ENERGY VALUE (E) | DETECTION TIME (T) |
|---|---|---|---|
| D1 | P11 | E11 | T11 |
| | P12 | E12 | T12 |
| | P13 | E13 | T13 |
| | ⋮ | ⋮ | ⋮ |

| MODULE ID | SCINTILLATOR NUMBER (P) | ENERGY VALUE (E) | DETECTION TIME (T) |
|---|---|---|---|
| D2 | P21 | E21 | T21 |
| | P22 | E22 | T22 |
| | P23 | E23 | T23 |
| | ⋮ | ⋮ | ⋮ |

| MODULE ID | SCINTILLATOR NUMBER (P) | ENERGY VALUE (E) | DETECTION TIME (T) |
|---|---|---|---|
| D3 | P31 | E31 | T31 |
| | P32 | E32 | T32 |
| | P33 | E33 | T33 |
| | ⋮ | ⋮ | ⋮ |

| COINCIDENCE NUMBER | SCINTILLATOR NUMBER (P) | ENERGY VALUE (E) | DETECTION TIME (T) | SCINTILLATOR NUMBER (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

MEDICAL IMAGE PROCESSING APPARATUS, AND NUCLEAR MEDICINE DIAGNOSIS APPARATUS

CROSS-REFERENCE TO RELATED APPLICATIONS

This application is based upon and claims the benefit of priority from Japanese Patent Application No. 2019-132849, filed on Jul. 18, 2019; the entire contents of which are incorporated herein by reference.

FIELD

Embodiments described herein relate generally to a medical image processing apparatus, and a nuclear medicine diagnosis apparatus.

BACKGROUND

The Time of Flight (TOF) technology has advanced in Time-of-Flight Positron Emission computed Tomography (TOF-PET) apparatuses. For example, a technique is known by which a TOF-PET apparatus is configured to generate TOF depiction image data representing a TOF depiction image in which annihilation points indicating the positions of occurrence of annihilation events are depicted as points or a line. The lower the time resolution is, the longer is the length of the line depicted as the annihilation point in the TOF depiction image. Conversely, the higher the time resolution is, the shorter is the length of the line depicted as the annihilation point in the TOF depiction image. In other words, the closer the time indicating the time resolution is to 0 psec, the closer to 0 the length of the line is.

Even when the time resolution of a detector system is sufficiently high (e.g., the time indicating the time resolution is 100 psec or lower), the level of precision regarding the positions of occurrence of annihilation events indicated by TOF depiction images is not excellent due to various effects as explained below.

For example, TOF depiction images are each an image in which, on a Line of Response (LOR) between two detectors configured to detect a pair of annihilation gamma rays, an annihilation point is depicted in the position of occurrence of an annihilation event corresponding to the time difference of the detections. For this reason, when TOF depiction image data is generated, it is difficult to eliminate, for example, effects of gamma-ray absorption and scattering within the examined subject and of two gamma rays that were accidentally detected substantially at the same time although the gamma rays are not a pair of annihilation gamma rays. Accordingly, due to these various effects, the level of precision regarding the position of occurrence of the annihilation events indicated in TOF depiction images is not excellent.

Consequently, even after TOF depiction image data is generated, it would be desirable, after all, to generate reconstructed PET image data suppressing these effects, by performing a normal image reconstruction process that involves a correcting process to suppress the effects, for example, of the gamma-ray absorption and scattering and of the two gamma rays that were detected substantially at the same time.

However, the normal image reconstructing process implementing a successive approximation reconstruction method or the like requires an enormous amount of calculations, and the reconstruction of the reconstructed PET image data therefore takes a long period of time.

BRIEF DESCRIPTION OF THE DRAWINGS

FIG. 9 is a table for explaining an example of a time-series list of coincidence counting information according to the first embodiment;

DETAILED DESCRIPTION

A medical image processing apparatus according to an embodiment includes processing circuitry. The processing circuitry is configured to obtain Time-of-Flight (TOF) depiction image data generated on the basis of an annihilation point of a gamma ray. The processing circuitry is configured to output reconstructed Positron Emission computed Tomography (PET) image data on the basis of the TOF depiction image data and a trained model that outputs the reconstructed PET image data on the basis of an input of the TOF depiction image data.

The following will describe exemplary embodiments of a medical image processing apparatus, a medical image diagnosis apparatus, and a nuclear medicine diagnosis apparatus in detail, with reference to the accompanying drawings. In the following sections, a PET-CT apparatus will be explained as an example of the medical image diagnosis apparatus and the nuclear medicine diagnosis apparatus. Further, the medical image processing apparatus, the medical image diagnosis apparatus, and the nuclear medicine diagnosis apparatus of the present disclosure are not limited to the embodiments described below.

First Embodiment

Figure 1:
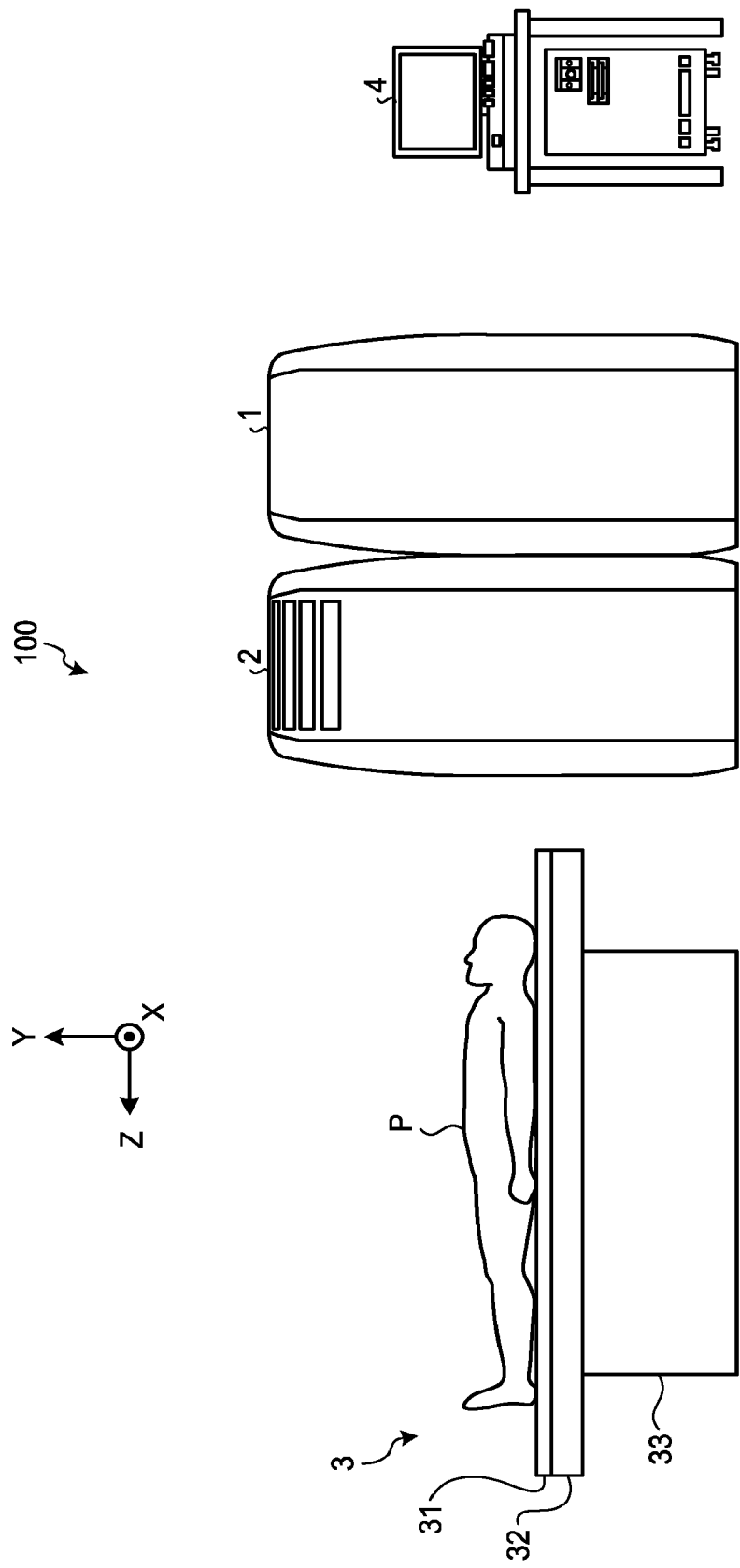
FIG. 1 is a drawing illustrating an example of an overall configuration of a PET Computed Tomography (PET-CT) apparatus according to a first embodiment.

To begin with, an overall configuration of a PET Computed Tomography (PET-CT) apparatus 100 according to a first embodiment will be explained, with reference to FIG. 1. FIG. 1 is a drawing illustrating an example of the overall configuration of the PET-CT apparatus 100 according to the first embodiment. As illustrated in FIG. 1, the PET-CT apparatus 100 according to the first embodiment includes a PET gantry device 1, a CT gantry device 2, a couch 3, and a console device 4. A drug (a radioactive medicine) labeled with a positron emission nucleus has been administered for a subject P.

Figure 2:
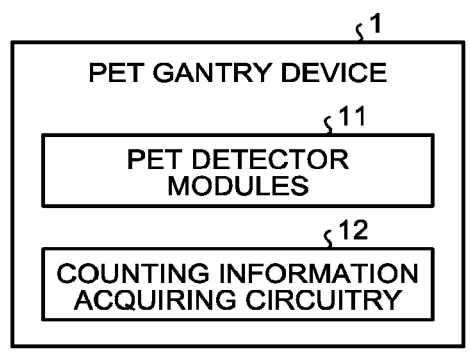
FIG. 2 is a diagram illustrating an exemplary configuration of a PET gantry device according to the first embodiment.
Figure 3:
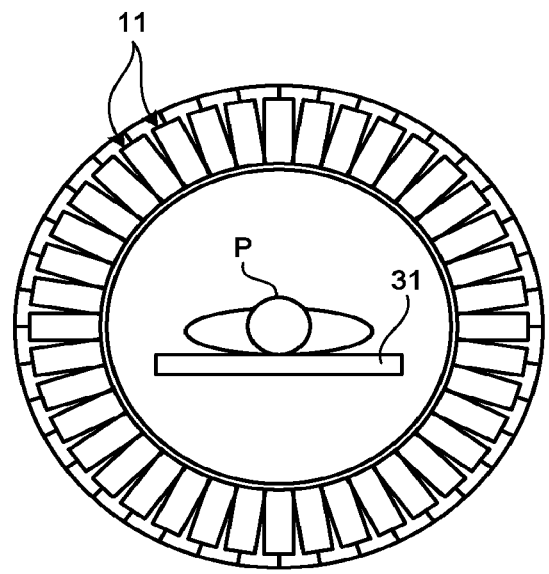
FIG. 3 is a drawing illustrating an exemplary configuration of the PET gantry device according to the first embodiment.

The PET gantry device 1 is an apparatus configured to acquire counting information, by detecting a pair of gamma rays (annihilation gamma rays) emitted from a biological tissue that has taken in the positron emission nucleus and generating the counting information from a detection signal of the gamma rays. FIGS. 2 and 3 are drawings illustrating exemplary configurations of the PET gantry device 1 according to the first embodiment.

As illustrated in FIG. 2, the PET gantry device 1 includes PET detector modules 11 and counting information acquiring circuitry 12. For example, as illustrated in FIG. 3, in the PET gantry device 1, the plurality of PET detector modules 11 are arranged so as to enclose the surrounding of the subject P in a ring formation. The PET detector modules 11 are configured to convert gamma rays emitted from the inside of the subject P into light and to further convert the light into an electrical signal (the detection signal). Further, the PET detector modules 11 are configured to transmit the detection signal to the counting information acquiring circuitry 12.

The counting information acquiring circuitry 12 is configured to generate the counting information from the detection signal output by the PET detector modules 11 and to store the generated counting information into storage circuitry 41a (explained later) of the console device 4.

Figures 4, 5:
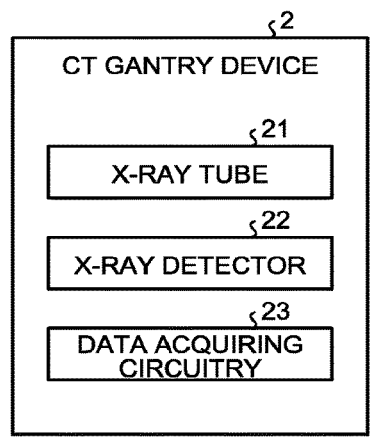
FIG. 4 is a drawing illustrating an example of counting information according to the first embodiment.
FIG. 5 is a diagram illustrating an exemplary configuration of a CT gantry device according to the first embodiment.

For example, the counting information acquiring circuitry 12 is configured to acquire the counting information by generating the counting information from the detection signal output by the PET detector modules 11. The counting information includes detection positions, energy values, and detection times of the gamma rays. FIG. 4 is a drawing illustrating an example of the counting information according to the first embodiment. For example, as illustrated in FIG. 4, the counting information includes scintillator numbers (P), energy values (E), and detection times (T). In the counting information, the scintillator numbers (P), the energy values (E), and the detection times (T) are kept in correspondence with module IDs identifying the PET detector modules 11.

Returning to the description of FIG. 1, the CT gantry device 2 according to the present embodiment is an apparatus configured to generate X-ray projection data from which CT image data (X-ray CT image data) is derived, by detecting X-rays that have passed through the subject P. Further, the CT gantry device 2 is capable of generating X-ray projection data from which a two- or three-dimensional scanogram is derived.

FIG. 5 is a diagram illustrating an exemplary configuration of the CT gantry device 2 according to the first embodiment. As illustrated in FIG. 5, the CT gantry device 2 includes an X-ray tube 21, an X-ray detector 22, and data acquiring circuitry 23. The X-ray tube 21 is a device configured to generate an X-ray beam and to radiate the generated X-ray beam onto the subject P. The X-ray detector 22 is a device configured to detect, in a position opposing the X-ray tube 21, the X-rays that have passed through the subject P. More specifically, the X-ray detector 22 is a two-dimensional array detector configured to detect data of a two-dimensional intensity distribution (two-dimensional X-ray intensity distribution data) of the X-rays that have passed through the subject P. Even more specifically, in the X-ray detector 22, a plurality of rows of detecting elements each including a plurality of X-ray detecting elements corresponding to a plurality of channels are arranged along the body axis direction of the subject P. On the inside of the CT gantry device 2, the X-ray tube 21 and the X-ray detector 22 are supported by a rotating frame (not illustrated).

The data acquiring circuitry 23 is a Data Acquisition System (DAS) and is configured to generate X-ray projection data by performing an amplifying process, an Analog to Digital (A/D) converting process, and the like on the two-dimensional X-ray intensity distribution data detected by the X-ray detector 22. Further, the data acquiring circuitry 23 is configured to transmit the X-ray projection data to the console device 4 illustrated in FIG. 1.

Returning to the description of FIG. 1, the couch 3 is a bed on which the subject P is placed and includes a couchtop 31, a supporting frame 32, and a couch device 33. On the basis of an instruction received from an operator of the PET-CT apparatus 100 via the console device 4, the couch 3 is configured to sequentially move the subject P to each of the image taking openings of the CT gantry device 2 and the PET gantry device 1. In other words, by controlling the couch 3, the PET-CT apparatus 100 at first takes CT image data and subsequently takes PET image data. Although FIG. 1 illustrates the example in which the CT gantry device 2 is arranged on the couch 3 side, possible embodiments are not limited to this example. The PET gantry device 1 may be arranged on the couch 3 side.

By employing a driving mechanism (not illustrated), the couch 3 is configured to move the couchtop 31 and the supporting frame 32 in a central axis direction of the detectors' fields of vision of the CT gantry device 2 and the PET gantry device 1. In other words, the couch 3 is configured to move the couchtop 31 and the supporting frame 32 in the direction along the longitudinal direction of the couchtop 31 and the supporting frame 32.

Figure 6:
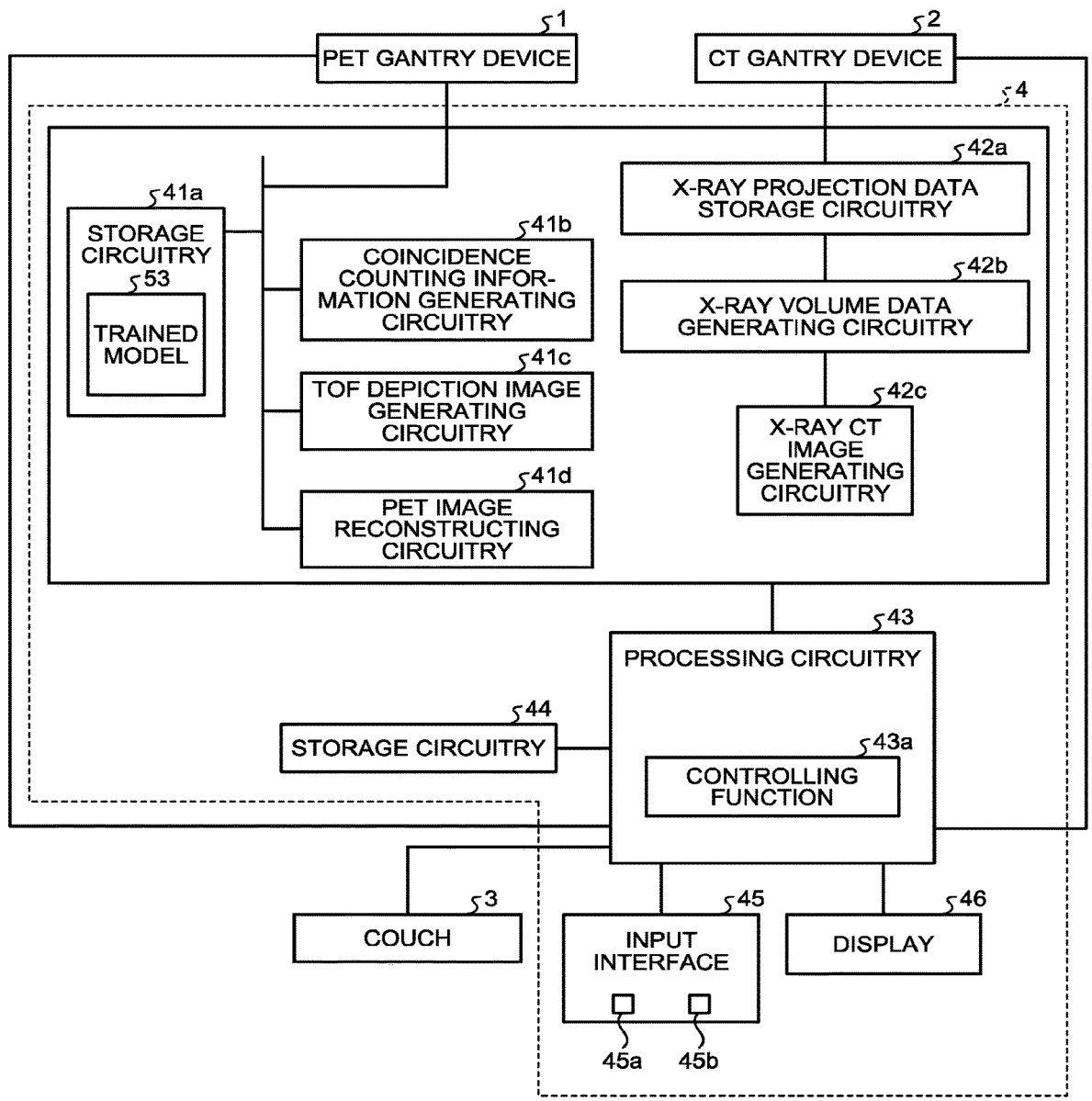
FIG. 6 is a diagram illustrating an exemplary configuration of a console device according to the first embodiment.

The console device 4 is a device configured to receive instructions from the operator and to control processes performed by the PET-CT apparatus 100. FIG. 6 is a diagram illustrating an exemplary configuration of the console device 4 according to the first embodiment. As illustrated in FIG. 6, the console device 4 includes the storage circuitry 41a, coincidence counting information generating circuitry 41b, TOF depiction image generating circuitry 41c, PET image reconstructing circuitry 41d, X-ray projection data storage circuitry 42a, X-ray volume data generating circuitry 42b, X-ray CT image generating circuitry 42c, processing circuitry 43, storage circuitry 44, an input interface 45, and a display 46.

The storage circuitry 41a is configured to store therein the counting information transmitted thereto from the PET gantry device 1. The counting information is to be used in a process performed by the coincidence counting information generating circuitry 41b. After being used in the process performed by the coincidence counting information generating circuitry 41b, the counting information stored in the storage circuitry 41a may be deleted from the storage circuitry 41a. Alternatively, the counting information stored in the storage circuitry 41a may be deleted after having been saved for a certain period of time.

Further, the storage circuitry 41a is configured to store therein coincidence counting information (explained later) generated by the coincidence counting information generating circuitry 41b. Further, the storage circuitry 41a is configured to store therein TOF depiction image data (explained later) generated by the TOF depiction image generating circuitry 41c. In addition, the storage circuitry 41a is configured to store therein reconstructed PET image data (explained later) derived by the PET image reconstructing circuitry 41d. The storage circuitry 41a is realized by using a semiconductor memory element such as a flash memory, or a hard disk, an optical disk, or the like. The storage circuitry 41a is an example of a storage unit.

Further, in the present embodiment, the storage circuitry 41a is configured to store therein a trained model 53. For example, the trained model 53 is generated by an external device such as a server. The external device that generates the trained model 53 may be referred to as a trained model generating device. Alternatively, the trained model 53 may be generated by the console device 4.

Figure 7:
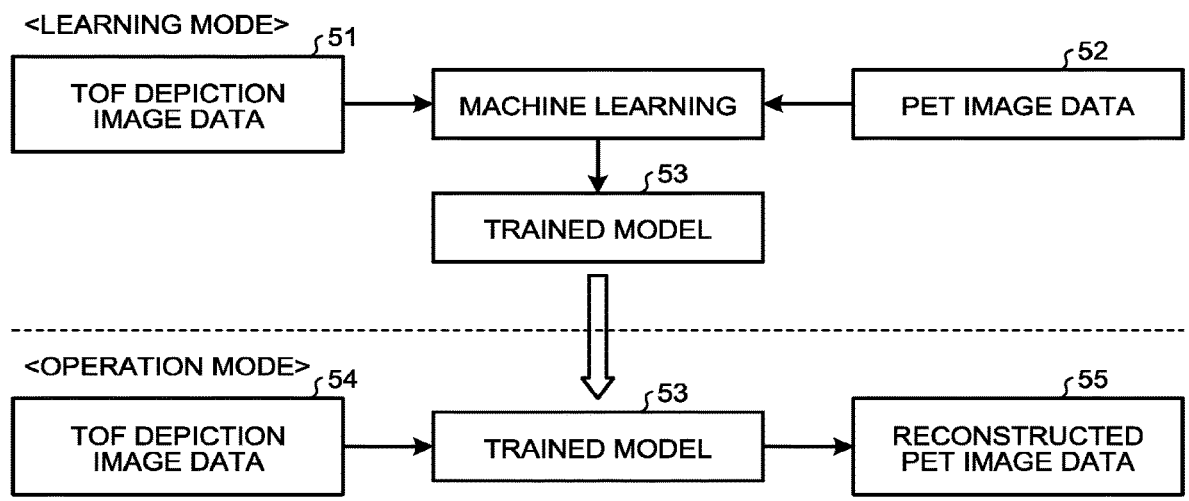
FIG. 7 is a chart for explaining examples of a process in a learning mode and a process in an operation mode according to the first embodiment.

The trained model 53 will be explained with reference to FIG. 7. FIG. 7 is a chart for explaining examples of a process in a learning mode and a process in an operation mode according to the first embodiment. As illustrated in FIG. 7, in the learning mode, the trained model generating device is configured to generate the trained model 53 by learning a relationship between TOF depiction image data 51 and PET image data 52.

Figure 8A:
FIG. 8A is a drawing illustrating an example of a TOF depiction image represented by TOF depiction image data according to the first embodiment.
Figure 8B:
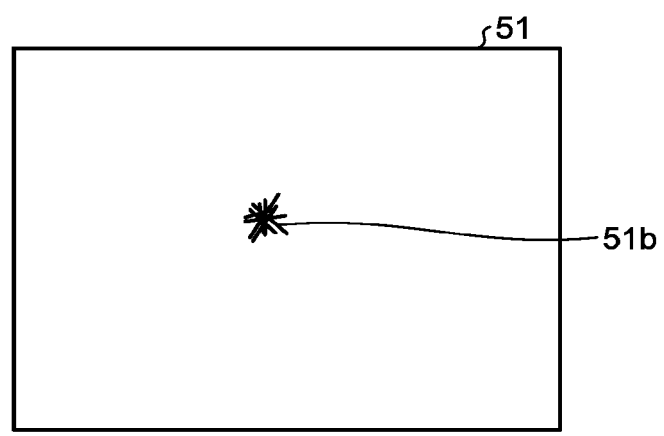
FIG. 8B is a drawing illustrating another example of a TOF depiction image represented by TOF depiction image data according to the first embodiment.

Next, an example of the TOF depiction image data 51 will be explained. FIGS. 8A and 8B are drawing illustrating examples of TOF depiction images represented by the TOF depiction image data 51 according to the first embodiment.

The TOF depiction image data 51 illustrated in FIG. 8A represents a TOF depiction image that depicts annihilation points 51a indicating positions of occurrence of annihilation events as points. The TOF depiction image data 51 illustrated in FIG. 8B represents a TOF depiction image that depicts annihilation points 51b indicating positions of occurrence of annihilation events as lines.

To generate the trained model 53, pieces of TOF depiction image data 51 having a plurality of mutually-different noise levels are used. For example, with a plurality of mutually-different scan times, a plurality of pieces of coincidence counting information from which a plurality of TOF depiction image data 51 are derived are acquired. Further, to acquire the plurality of pieces of coincidence counting information, a plurality of mutually-different types of drugs may be administered for the subject P, respectively. Alternatively, to acquire the plurality of pieces of coincidence counting information, a drug may be administered for the subject P in a plurality of mutually-different amounts, respectively. From the plurality of pieces of coincidence counting information acquired in this manner, the pieces of TOF depiction image data 51 having the plurality of mutually-different noise levels are acquired.

The PET image data 52 is image data reconstructed by implementing a successive approximation reconstruction method, while using the coincidence counting information from which the TOF depiction image data 51 is derived. In this situation, examples of the successive approximation reconstruction method include a Maximum Likelihood Expectation Maximization (MLEM) method and an Ordered Subset MLEM (OSEM) method by which convergence time is significantly shortened by improving an algorithm of the MLEM method.

On the basis of TOF depiction image data 54, the trained model 53 is configured to output reconstructed PET image data 55, which is image data corresponding to the PET image data 52.

In other words, the trained model generating device is configured to generate the trained model 53, by learning the TOF depiction image data 51 and the PET image data 52 that are kept in correspondence with each other. The trained model 53 is configured to receive an input of the TOF depiction image data 54 and to output the reconstructed PET image data 55, which is image data corresponding to the PET image data 52. The trained model 53 is a trained model generated by learning the plurality of pieces of TOF depiction image data 54 having a plurality of mutually-different noise levels.

For example, the trained model generating device is configured to perform machine learning, by inputting, to a machine learning engine, a set made up of the TOF depiction image data 51 and the PET image data 52 as learning-purpose data (training data).

For example, the machine learning engine is configured to perform the machine learning by using any of various types of algorithms such as those of Deep Learning, a neural network, a logistic regression analysis, a non-linear discriminant analysis, a Support Vector Machine (SVM), a random forest, Naive Bayes, and the like.

As a result of the machine learning described above, the trained model generating device generates the trained model 53. Further, the trained model 53 is stored into the storage circuitry 41a. Processes in the operation mode will be explained later.

Returning to the description of FIG. 6, the coincidence counting information generating circuitry 41b is configured to generate a time-series list of the coincidence counting information, by using a plurality of pieces of counting information stored in the storage circuitry 41a. For example, in the plurality of pieces of counting information, the coincidence counting information generating circuitry 41b is configured to search for sets of counting information in each of which a pair of annihilation gamma rays are counted substantially at the same time, on the basis of the detection times (T) of the counting information. After that, the coincidence counting information generating circuitry 41b is configured to generate a piece of coincidence counting information for each set of counting information resulting from the search, to arrange the generated pieces of coincidence counting information approximately in a time series, and to store the pieces of coincidence counting information into the storage circuitry 41a. The coincidence counting information generating circuitry 41b is realized by using a processor, for example.

FIG. 9 is a table for explaining an example of the time-series list of the coincidence counting information according to the first embodiment. As illustrated in FIG. 9, the storage circuitry 41a is configured to store therein the sets of counting information so as to be kept in correspondence with "Coincidence Numbers", which are serial numbers of the coincidence counting information. In the first embodiment, in the time-series list of the coincidence counting information, the information is arranged approximately in a time series on the basis of the detection times (T) of the counting information.

For example, the coincidence counting information generating circuitry 41b is configured to generate the coincidence counting information on the basis of a condition (a coincidence counting information generating condition) used at the time of generating the coincidence counting information and input by an operator. The coincidence counting information generating condition designates a time window width. For example, on the basis of the time window width, the coincidence counting information generating circuitry 41b generates the coincidence counting information. In this manner, by generating the coincidence counting information, the coincidence counting information generating circuitry 41b acquires the coincidence counting information.

For example, by referring to the storage circuitry 41a, the coincidence counting information generating circuitry 41b searches for a set made up of such pieces of counting information of which the time difference between the detection times (T) falls within the time window width, among the PET detector modules 11. For example, as a set satisfying the coincidence counting information generating condition, the coincidence counting information generating circuitry 41b finds a set made up of "P11, E11, and T11" and "P22, E22, and T22" in the search, further generates the set as coincidence counting information, and stores the coincidence counting information into the storage circuitry 41a. In this situation, the coincidence counting information generating circuitry 41b may generate the coincidence counting information by using an energy window width together with the time window width. Further, the coincidence counting information generating circuitry 41b may be provided in the PET gantry device 1.

On the basis of the time-series list of the coincidence counting information stored in the storage circuitry 41a, the TOF depiction image generating circuitry 41c is configured to generate TOF depiction image data representing a TOF depiction image in which the annihilation points indicating the positions of occurrence of the annihilation events are depicted as points or lines. In other words, the TOF depiction image generating circuitry 41c is configured to acquire the TOF depiction image data. For example, the TOF depiction image generating circuitry 41c is realized by using a processor. The TOF depiction image generating circuitry 41c is an example of an acquiring unit.

Figure 10:
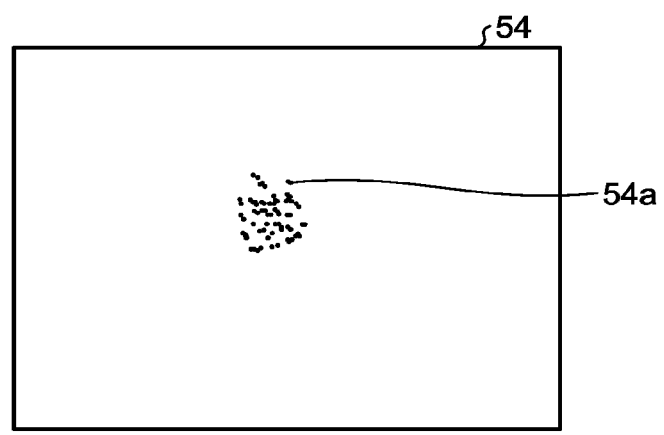
FIG. 10 is a drawing illustrating an example of a TOF depiction image represented by TOF depiction image data generated by TOF depiction image generating circuitry according to the first embodiment.

FIG. 10 is a drawing illustrating an example of the TOF depiction image represented by the TOF depiction image data generated by the TOF depiction image generating circuitry 41c according to the first embodiment. As illustrated in FIG. 10, for example, the TOF depiction image generating circuitry 41c is configured to generate the TOF depiction image data 54 representing a TOF depiction image in which annihilation points 54a are depicted as points. In other words, on the basis of the annihilation points 54a, the TOF depiction image generating circuitry 41c is configured to generate the TOF depiction image data 54. After that, the TOF depiction image generating circuitry 41c is configured to store the TOF depiction image data 54 into the storage circuitry 41a. The TOF depiction image data 54 stored in the storage circuitry 41a is to be used in a process performed by the PET image reconstructing circuitry 41d. Further, the TOF depiction image generating circuitry 41c is configured to output the TOF depiction image data 54 to the processing circuitry 43.

The PET image reconstructing circuitry 41d is capable of obtaining reconstructed PET image data by implementing two types of methods. Further, the PET image reconstructing circuitry 41d is configured to transmit the obtained reconstructed PET image data to the processing circuitry 43.

A first type of method will be explained. For example, when a switch button 45a (explained later) of the input interface 45 is in an ON state, the PET image reconstructing circuitry 41d is configured to read the time-series list of the coincidence counting information stored in the storage circuitry 41a and to reconstruct reconstructed PET image data by implementing a successive approximation reconstruction method, while using the read time-series list. Examples of the successive approximation reconstruction method include the MLEM method and the OSEM method. After that, the PET image reconstructing circuitry 41d is configured to store the reconstructed PET image data that has been reconstructed, into the storage circuitry 41a.

Next, a second type of method will be explained. For example, when a switch button 45b (explained later) of the input interface 45 is in an ON state, the PET image reconstructing circuitry 41d is configured to read the TOF depiction image data 54 stored in the storage circuitry 41a. After that, as previously described as the process in the operation mode with reference to FIG. 7, the PET image reconstructing circuitry 41d is configured to cause the trained model 53 to output the reconstructed PET image data 55, by inputting the TOF depiction image data 54 to the trained model 53 stored in the storage circuitry 41a. Subsequently, the PET image reconstructing circuitry 41d is configured to obtain the reconstructed PET image data 55 output from the trained model 53. In other words, on the basis of the TOF depiction image data 54 and the trained model 53, the PET image reconstructing circuitry 41d is configured to output the reconstructed PET image data 55. The PET image reconstructing circuitry 41d has thus derived the reconstructed PET image data 55. For example, the PET image reconstructing circuitry 41d is realized by using a processor. The PET image reconstructing circuitry 41d is an example of a processing unit.

The X-ray projection data storage circuitry 42a is configured to store therein the X-ray projection data transmitted thereto from the data acquiring circuitry 23. More specifically, the X-ray projection data storage circuitry 42a is configured to store therein the X-ray projection data used at the time of reconstructing scanograms and CT images.

The X-ray volume data generating circuitry 42*b* is configured to reconstruct X-ray volume data, by performing a reconstructing process on the X-ray projection data stored in the X-ray projection data storage circuitry 42*a*, by implementing a Filtered Back Projection (FBP) method or the successive approximation reconstruction method, for example.

The X-ray CT image generating circuitry 42*c* is configured to generate CT image data representing a CT image indicating a plurality of cross-sectional planes orthogonal to the body axis direction of the subject P, by performing an image generating process on the X-ray volume data generated by the X-ray volume data generating circuitry 42*b*, on the basis of an image taking condition (e.g., a slice width) determined in an image taking plan. After that, the X-ray CT image generating circuitry 42*c* is configured to transmit the generated CT image data to the processing circuitry 43.

Further, the X-ray CT image generating circuitry 42*c* is configured to generate a scanogram used for determining the position of the subject P or the like, by performing an image generating process on the X-ray volume data generated by the X-ray volume data generating circuitry 42*b*. Further, the X-ray CT image generating circuitry 42*c* is configured to transmit the generated scanogram to the processing circuitry 43.

The processing circuitry 43 includes a controlling function 43*a*. The controlling function 43*a* is configured to control the entirety of processes performed by the PET-CT apparatus 100. For example, the controlling function 43*a* is configured to receive instructions from the operator via the input interface 45 and to execute processes related to acquiring scanograms, performing scans (main image taking processes), reconstructing images, generating images, and displaying images, by controlling the PET gantry device 1, the CT gantry device 2, and the couch 3 according to the received instructions. For example, the processing circuitry 43 is configured to execute the processes by reading and executing a computer program (hereinafter, "program") corresponding to the controlling function 43*a*, from the storage circuitry 44.

For example, upon receipt of the TOF depiction image data 54 transmitted thereto by the TOF depiction image generating circuitry 41*c*, the controlling function 43*a* is configured to store the received TOF depiction image data 54 into the storage circuitry 44. Further, upon receipt of the reconstructed PET image data transmitted thereto by the PET image reconstructing circuitry 41*d*, the controlling function 43*a* is configured to store the received reconstructed PET image data into the storage circuitry 44. Further, upon receipt of the CT image data transmitted thereto by the X-ray CT image generating circuitry 42*c*, the controlling function 43*a* is configured to store the received CT image data into the storage circuitry 44. Furthermore, upon receipt of the scanogram transmitted thereto by the X-ray CT image generating circuitry 42*c*, the controlling function 43*a* is configured to store the received scanogram into the storage circuitry 44.

The storage circuitry 44 is configured to store therein data used when the processing circuitry 43 controls the entirety of the processes performed by the PET-CT apparatus, the TOF depiction image data 54, the reconstructed PET image data, the CT image data, the scanogram, and the like. Further, the storage circuitry 44 is configured to store therein programs executed by the processing circuitry 43.

The input interface 45 is realized by using a trackball, a switch button, a mouse, a keyboard, a touchpad on which an input operation is performed by touching an operation surface thereof, a touch monitor in which a display screen and a touchpad are integrally formed, a contactless input circuit using an optical sensor, an audio input circuit, and/or the like, used for establishing various types of settings. The input interface 45 is connected to the processing circuitry 43 and is configured to convert an input operation received from the operator into an electrical signal and to output the electrical signal to the processing circuitry 43. In the present disclosure, the input interface 45 does not necessarily have to include physical operation component parts such as a mouse, a keyboard, and/or the like. Possible examples of the input interface include electrical signal processing circuitry configured to receive an electrical signal corresponding to an input operation from an external input device provided separately from the apparatus and to output the received electrical signal to the processing circuitry 43.

The input interface 45 includes the switch button 45*a* and the switch button 45*b*. By pressing one of the switch buttons, namely the switch buttons 45*a* and 45*b*, the operator is able to cause the pressed switch button to be in the ON state. The switch button 45*a* is a switch button for causing the PET image reconstructing circuitry 41*d* to reconstruct the reconstructed PET image data by implementing the successive approximation reconstruction method. In contrast, the switch button 45*b* is a button for causing the PET image reconstructing circuitry 41*d* to derive the reconstructed PET image data 55 by employing the trained model 53. As described herein, the input interface 45 is an interface capable of selecting whether the PET image reconstructing circuitry 41*d* is caused to reconstruct the reconstructed PET image data by implementing the successive approximation reconstruction method or to derive the reconstructed PET image data by using the TOF depiction image data 54.

The display 46 is configured to display a Graphical User Interface (GUI) used by the operator of the PET-CT apparatus 100 for inputting various types of setting requests through the input interface 45. Further, under display control exercised by the controlling function 43*a*, the display 46 is configured to display a TOF depiction image represented by the TOF depiction image data 54, the reconstructed PET image represented by the reconstructed PET image data, the CT image represented by the CT image data, the scanogram, and the like generated by the console device 4. Further, the display 46 is configured to display various types of messages and display information, to notify the operator of processing statuses and processing results. Furthermore, the display 46 includes a speaker and is also capable of outputting audio.

Figure 11:
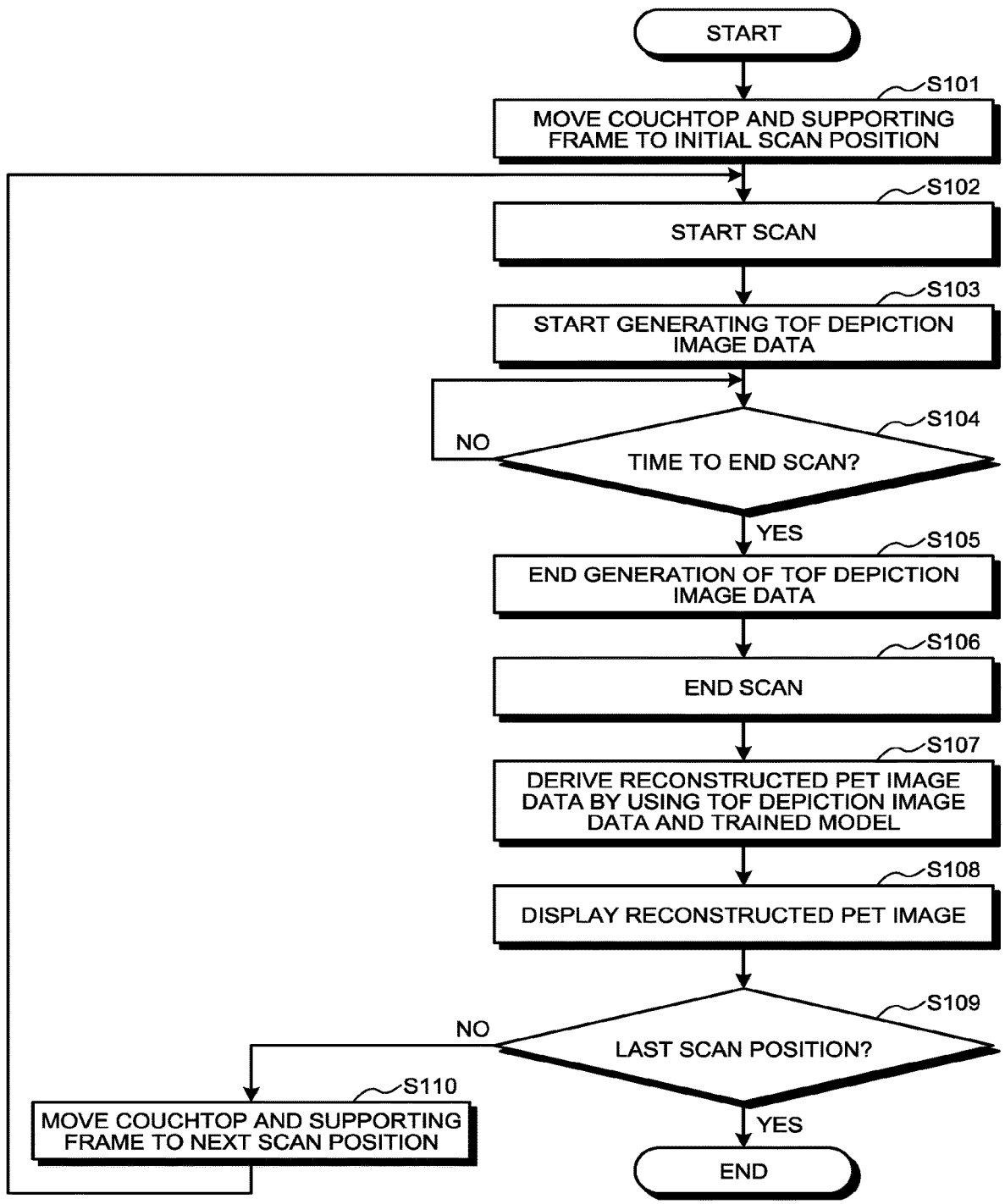
FIG. 11 is a flowchart illustrating an example of a flow in a process performed by the PET-CT apparatus according to the first embodiment.

FIG. 11 is a flowchart illustrating an example of a flow in a process performed by the PET-CT apparatus 100 according to the first embodiment. The process in FIG. 11 is a process performed when the switch button 45*b* is in the ON state. Further, the process in FIG. 11 is a process performed to acquire coincidence counting information with respect to each of sections of the subject P, by implementing a step-and-shoot method by which each of the sections of the subject P is scanned while moving, in steps, the couchtop 31 on which the subject P is placed in the longitudinal direction of the couchtop 31. In the process in FIG. 11, the couchtop 31 is moved to each of a plurality of scan positions. Further, in the process in FIG. 11, the coincidence counting information is acquired in each of the plurality of scan positions.

As illustrated in FIG. 11, by controlling the driving mechanism described above, the controlling function 43*a* moves the couchtop 31 and the supporting frame 32 to an initial scan position (step S101). Further, by controlling the PET gantry device 1, the controlling function 43*a* starts a scan to acquire coincidence counting information, in the initial scan position (step S102).

After that, the TOF depiction image generating circuitry 41c starts generating the TOF depiction image data 54 on the basis of the acquired coincidence counting information (step S103).

Subsequently, the controlling function 43a judges whether or not it is time to end the scan performed in the initial scan position (step S104). When having determined that it is not time to end the scan (step S104: No), the controlling function 43a performs the judging process at step S104 again.

On the contrary, when it is determined that it is time to end the scan (step S104: Yes), the TOF depiction image generating circuitry 41c ends the generation of the TOF depiction image data 54 (step S105). As a result, a plurality of annihilation points detected between when the generation of the TOF depiction image data 54 was started at step S103 and when the generation of the TOF depiction image data 54 is ended at step S105 are depicted in the TOF depiction image data 54.

In this situation, the controlling function 43a may cause the display 46 to display, in a real-time manner, a TOF depiction image represented by the TOF depiction image data 54 in which annihilation points are sequentially added, in the duration from step S103 through step S105.

For example, in the TOF depiction image displayed on the display 46, annihilation points 54a are sequentially added. By viewing this TOF depiction image, the operator is able to roughly estimate the level of precision of the reconstructed PET image data being obtained.

Further, by controlling the PET gantry device 1, the controlling function 43a ends the scan to acquire the coincidence counting information, in the initial scan position (step S106). After that, by using the TOF depiction image data 54 and the trained model 53, the PET image reconstructing circuitry 41d derives the reconstructed PET image data 55 (step S107).

Subsequently, the controlling function 43a causes the display 46 to display the reconstructed PET image represented by the reconstructed PET image data 55 (step S108). Alternatively, at step S108, the controlling function 43a may cause the display 46 to display the TOF depiction image represented by the TOF depiction image data 54, together with the reconstructed PET image.

After that, the controlling function 43a judges whether or not the current scan position is the last scan position (step S109).

When it is determined that the current scan position is not the last scan position (step S109: No), the controlling function 43a moves the couchtop 31 and the supporting frame 32 to the next scan position by controlling the driving mechanism described above (step S110), and the process returns to step S102. Further, in the next scan position, the PET-CT apparatus 100 performs the same processes as those at steps S102 to S109 described as being performed in the initial scan position. Accordingly, the coincidence counting information is acquired with respect to each of the sections of the subject P. Further, the TOF depiction image data 54 is data based on the coincidence counting information acquired in this manner.

On the contrary, when it is determined that the current scan position is the last scan position (step S109: Yes), the controlling function 43a ends the process illustrated in FIG. 11.

Next, a process performed when the switch button 45a is in the ON state will be explained. In this situation, at step S107 of the process in FIG. 11, the PET image reconstructing circuitry 41d reconstructs the reconstructed PET image data by implementing the successive approximation reconstruction method, while using the time-series list of the coincidence counting information. The other processes at steps S101 through S106 and steps S108 through S110 are the same as the processes performed when the switch button 45b is in the ON state.

The PET-CT apparatus 100 according to the first embodiment has thus been explained. Instead of using the successive approximation reconstruction method which takes time between the start of the reconstruction of the reconstructed PET image data and the completion of the reconstruction, the PET-CT apparatus 100 according to the first embodiment is configured to derive the reconstructed PET image data by using the trained model 53 capable of obtaining the reconstructed PET image data in a shorter timer period than when the successive approximation reconstruction method is used. Accordingly, the PET-CT apparatus 100 according to the first embodiment is able to shorten the time period required by the acquisition of the reconstructed PET image data.

First Modification Example

In the first embodiment above, the example was explained in which the PET-CT apparatus 100 is configured to perform the scan to acquire the coincidence counting information by implementing the step-and-shoot method; however, the PET-CT apparatus 100 may perform a scan to acquire the coincidence counting information by implementing a continuous move method by which the scan is performed while the couchtop 31 on which the subject P is placed is being moved in the longitudinal direction. Thus, this modification example will be explained as a first modification example. The following description of the first modification example will primarily explain differences from the first embodiment.

Figure 12:
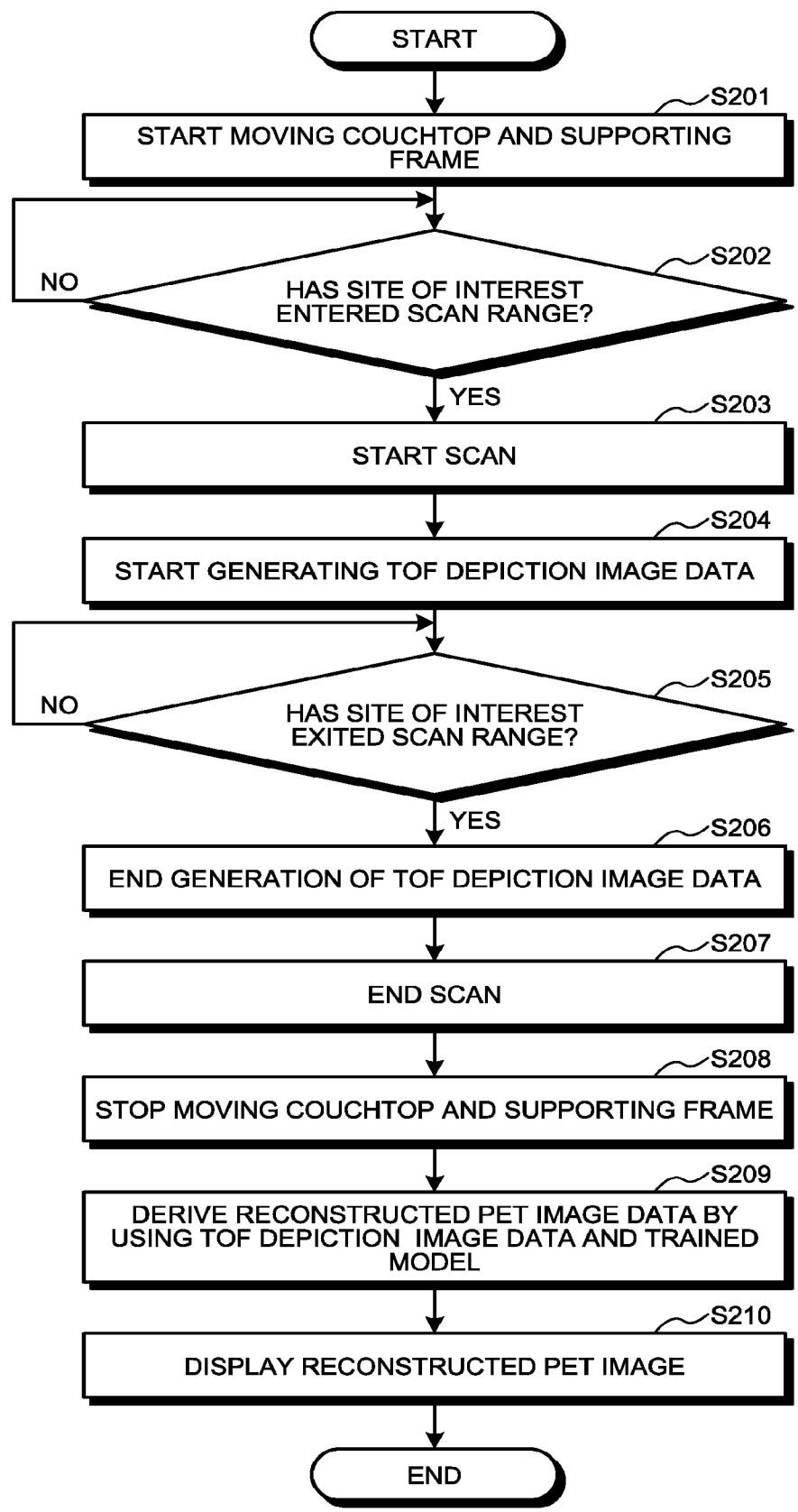
FIG. 12 is a flowchart illustrating an example of a flow in a process performed by a PET-CT apparatus according to a first modification example.
Figure 13:
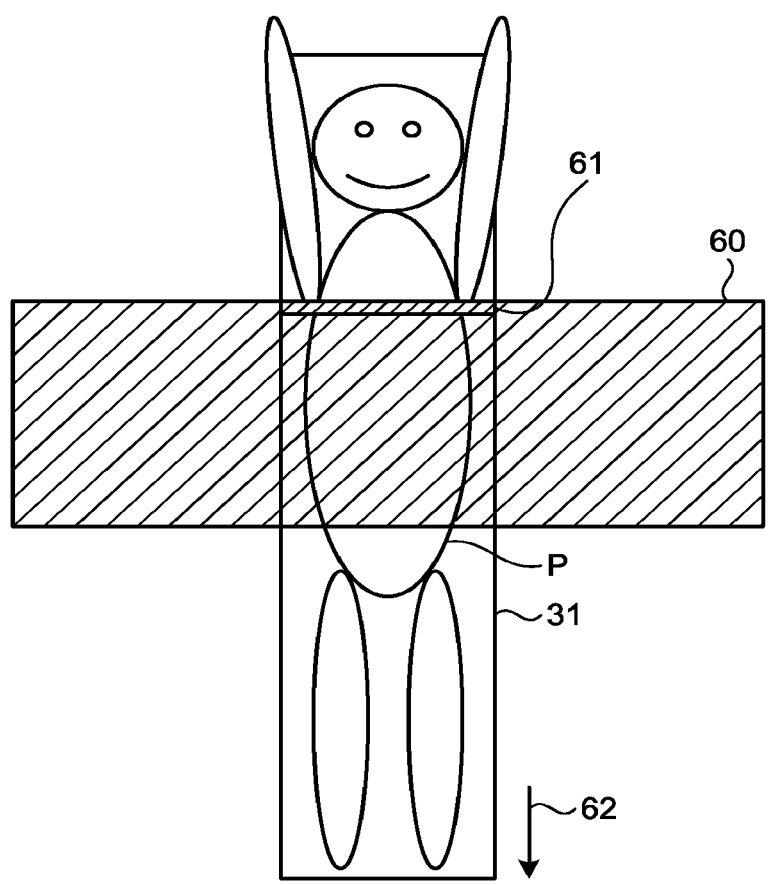
FIG. 13 is a drawing for explaining an example of a process performed by the PET-CT apparatus according to the first modification example.
Figure 14:
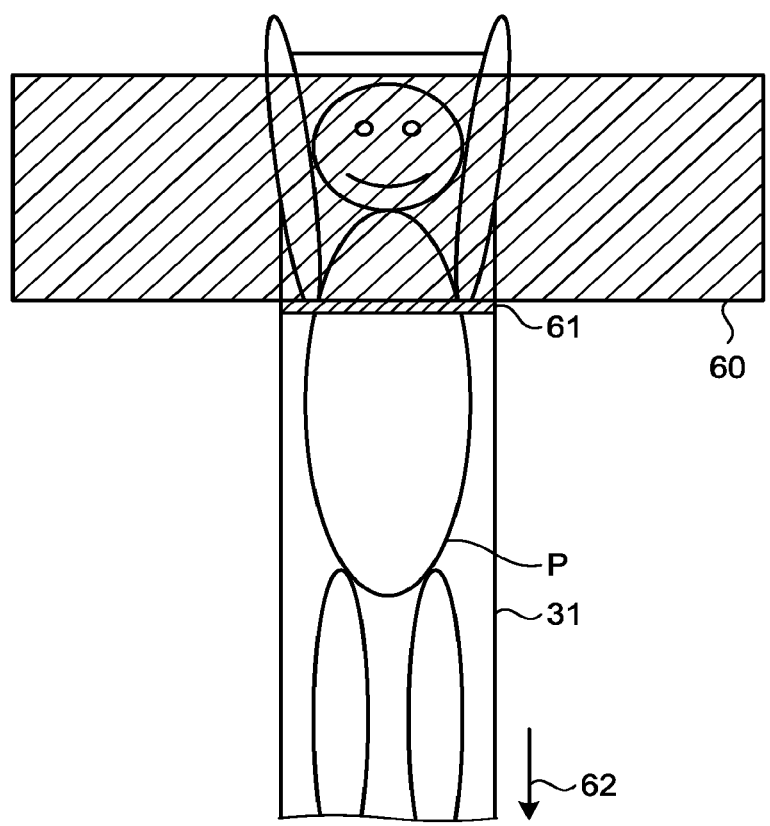
FIG. 14 is another drawing for explaining the example of the process performed by the PET-CT apparatus according to the first modification example.

FIG. 12 is a flowchart illustrating an example of a flow in a process performed by the PET-CT apparatus 100 according to the first modification example. FIGS. 13 and 14 are drawings for explaining an example of the process performed by the PET-CT apparatus 100 according to the first modification example. The process in FIG. 12 is a process performed when the switch button 45b is in the ON state. Also, the process in FIG. 12 is a process to acquire the coincidence counting information by implementing the continuous move method.

A scan range (a data acquisition range) 60 illustrated in FIGS. 13 and 14 is a range in which the PET gantry device 1 acquires the coincidence counting information. Further, a site of interest (a scanned site of interest) 61 is a site subject to a scan. For example, the site of interest 61 is set by the operator. Further, the direction indicated by an arrow 62 is the moving direction of the couchtop 31.

For example, FIG. 13 illustrates a positional relationship between the site of interest 61 and the scan range 60 at a time when the couchtop 31 on which the subject P is placed has moved in the direction indicated by the arrow 62 so that the site of interest 61 enters the scan range 60. Further, FIG. 14 illustrates a positional relationship between the site of interest 61 and the scan range 60 at a time when the couchtop 31 has further moved from the state indicated in FIG. 13 in the direction indicated by the arrow 62 so that the site of interest 61 exits the scan range 60.

By controlling the driving mechanism described above, the controlling function 43a moves the couchtop 31 and the supporting frame 32 so that the site of interest 61 is positioned on the subject P's head side relative to the scan range 60, and subsequently, as illustrated in FIG. 12, starts moving the couchtop 31 and the supporting frame 32 in the direction indicated by the arrow 62 (see FIG. 13) (step S201).

After that, as illustrated in FIG. 13, the controlling function 43a judges whether or not the site of interest 61 has entered the scan range 60 (step S202). When it is determined that the site of interest 61 has not entered the scan range 60 (step S202: No), the controlling function 43a performs the judging process at step S202 again.

On the contrary, when it is determined that the site of interest 61 has entered the scan range 60 (step S202: Yes), the controlling function 43a controls the PET gantry device 1 so as to start a scan to acquire coincidence counting information (step S203).

After that, the TOF depiction image generating circuitry 41c starts generating the TOF depiction image data 54 on the basis of the acquired coincidence counting information (step S204).

Subsequently, as illustrated in FIG. 14, the controlling function 43a judges whether or not the site of interest 61 has exited the scan range 60 (step S205). When it is determined that the site of interest 61 has not exited the scan range 60 (step S205: No), the controlling function 43a performs the judging process at step S205 again.

On the contrary, when it is determined that the site of interest 61 has exited the scan range 60 (step S205: Yes), the TOF depiction image generating circuitry 41c ends the generation of the TOF depiction image data 54 (step S206). As a result, a plurality of annihilation points detected between when the generation of the TOF depiction image data 54 was started at step S204 and when the generation of the TOF depiction image data 54 is ended at step S206 are depicted in the TOF depiction image data 54.

In this situation, the controlling function 43a may cause the display 46 to display, in a real-time manner, a TOF depiction image represented by the TOF depiction image data 54 in which annihilation points are sequentially added, in the duration from step S204 through step S206.

Subsequently, the controlling function 43a controls the PET gantry device 1 to end the scan to acquire the coincidence counting information (step S207). After that, the controlling function 43a controls the driving mechanism described above to stop the couchtop 31 and the supporting frame 32 (step S208).

Subsequently, the PET image reconstructing circuitry 41d derives the reconstructed PET image data 55 by using the TOF depiction image data 54 and the trained model 53 (step S209).

After that, the controlling function 43a causes the display 46 to display the reconstructed PET image represented by the reconstructed PET image data 55 (step S210), and the process in FIG. 12 is ended. At step S210, the controlling function 43a may cause the display 46 to display the TOF depiction image represented by the TOF depiction image data 54, together with the reconstructed PET image.

In the first modification example, the coincidence counting information is acquired while the subject P is moved relative to the PET gantry device 1. The TOF depiction image data 54 is data based on this coincidence counting information.

Next, a process performed when the switch button 45a is in the ON state will be explained. In this situation, at step S209 in the process in FIG. 12, the PET image reconstructing circuitry 41d reconstructs the reconstructed PET image data by implementing the successive approximation reconstruction method, while using the time-series list of the coincidence counting information. The other processes at steps S201 through S208, S209, and S210 are the same as the processes performed when the switch button 45b is in the ON state.

The PET-CT apparatus 100 according to the first modification example has thus been explained. The PET-CT apparatus 100 according to the first modification example is able to shorten the time period required by the acquisition of the reconstructed PET image data, similarly to the PET-CT apparatus 100 according to the first embodiment.

Second Modification Example

In the first modification example above, the example was explained in which the time at which the site of interest 61 has entered the scan range 60 is determined as the timing to start the scan, whereas the time at which the site of interest 61 has exited the scan range 60 is determined as the timing to end the scan; however, the timing to start the scan and the timing to end the scan may be other times. Accordingly, another example of the timing to start the scan and the timing to end the scan will be explained as a second modification example. The following description of the second modification example will primarily explain differences from the first embodiment and the first modification example.

Figure 15:
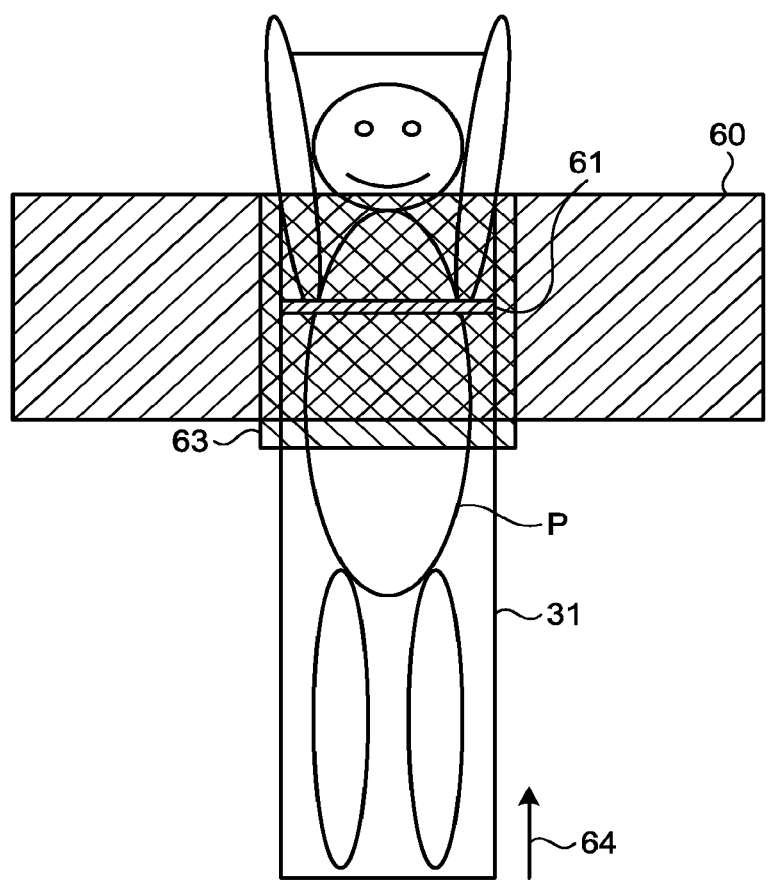
FIG. 15 is a drawing for explaining an example of a process performed by a PET-CT apparatus according to a second modification example.
Figure 16:
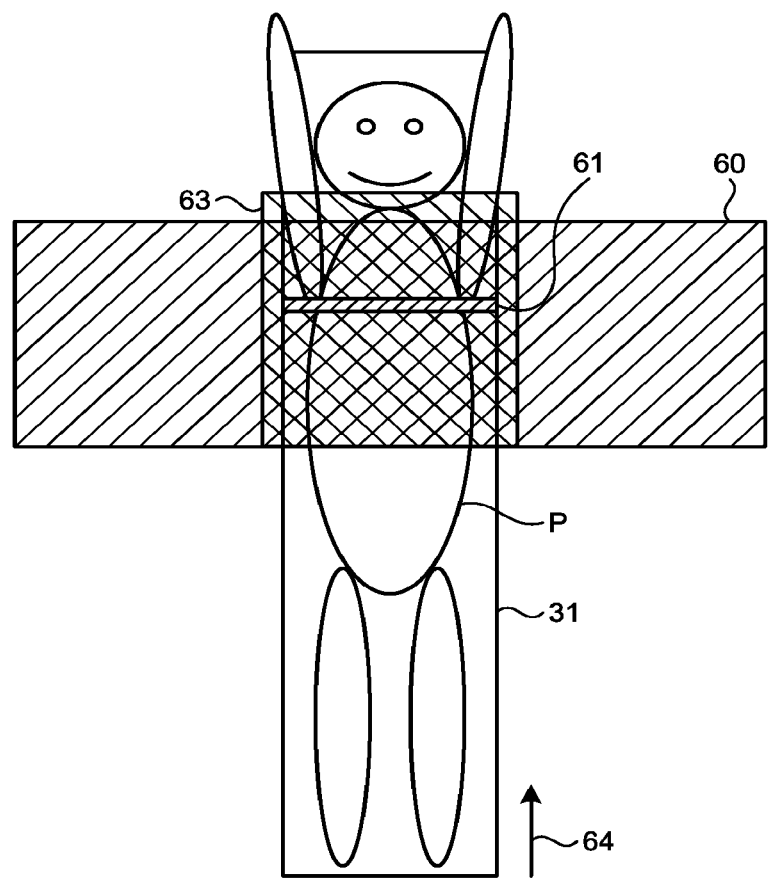
FIG. 16 is another drawing for explaining the example of the process performed by the PET-CT apparatus according to the second modification example.

FIGS. 15 and 16 are drawings for explaining an example of a process performed by the PET-CT apparatus 100 according to the second modification example. For instance, in the second modification example, the PET-CT apparatus 100 performs a scan to acquire the coincidence counting information by implementing the continuous move method, while the couchtop 31 is moving in the direction indicated by an arrow 64.

For example, as illustrated in FIG. 15, in some situations, the site of interest 61 may already be in the scan range (the data acquisition range) 60 at the beginning. In those situations, a scan is started at this point in time.

Further, when the couchtop 31 has moved from the state illustrated in FIG. 15 in the direction indicated by the arrow 64, the time at which, as illustrated in FIG. 16, the scan range 60 has reached the one end of a set scan range 63 positioned on the downstream side in terms of the direction indicated by the arrow 64 is determined as the timing to end the scan.

The PET-CT apparatus 100 according to the second modification example has thus been explained. The PET-CT apparatus 100 according to the second modification example is able to shorten the time period required by the acquisition of the reconstructed PET image data, similarly to the PET-CT apparatus 100 according to the first embodiment and the PET-CT apparatus 100 according to the first modification example.

In the first embodiment, the first modification example, and the second modification example, the example was explained in which the PET image reconstructing circuitry 41d is configured to derive the reconstructed PET image data 55, by using the TOF depiction image data 54 at the point in time when the scan is ended and the trained model 53; however, the PET image reconstructing circuitry 41d may derive the reconstructed PET image data 55 by using TOF depiction image data 54 at an arbitrary time between the start of the scan and the end of the scan, as well as the trained model 53.

Third Modification Example

In place of the trained model 53, a trained model corresponding to each of a plurality of sites of the subject P may be used. Thus, this modification example will be explained as a third modification example. The following description of the third modification example will primarily explain differences from the first embodiment.

Figure 17:
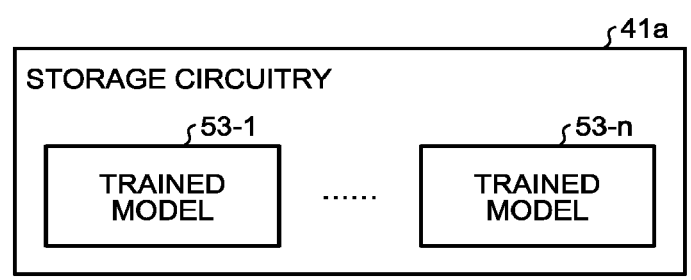
FIG. 17 is a diagram for explaining an example of a plurality of trained models according to a third modification example.

FIG. 17 is a drawing for explaining an example of a plurality of trained models 53-1 to 53-n (as many trained models as n where n is a natural number of 2 or larger) according to a third modification example. In the third modification example, for instance, FDG (18F-fluorodeoxyglucose) is administered for the subject P as a drug, for the purpose of finding cancer cells from the entire body. Each of the trained models 53-1 to 53-n is generated by learning a relationship between TOF depiction image data 51 based on coincidence counting information acquired by scanning a corresponding site and PET image data 52 based on the coincidence counting information. In the third modification example, the storage circuitry 41a has stored therein the trained models 53-1 to 53-n.

For example, separate trained models may be provided for the brain, the chest, the abdomen, the bladder, and the legs. More specifically, for example, when a reconstructed PET image representing the abdomen is compared with a reconstructed PET image representing the brain, the shape of the brain and the shape of the abdomen are different from each other. Further, when a reconstructed PET image representing the abdomen is compared with a reconstructed PET image representing the chest, because the chest has the heart, the shape of the abdomen and the shape of the chest are also different from each other. Further, when a reconstructed PET image representing the abdomen is compared with a reconstructed PET image representing the bladder, the pixel values in the section corresponding to the bladder are extremely higher than the pixel values in the section corresponding to the abdomen. Further, when a reconstructed PET image representing the abdomen is compared with a reconstructed PET image representing the legs, the shape of the abdomen and the shape of the legs are also different from each other. For this reason, when a trained model optimal for each of the sites is used, it is expected that the learning may be easier, convergence in the learning mode may be achieved earlier, and the quality of the acquired reconstructed PET image may be better.

In the third modification example, in the operation mode, the operator determines which one of the trained models 53-1 to 53-n is to receive an input of the TOF depiction image data 54. In this manner, in the third modification example, the operator determines the site corresponding to the TOF depiction image data 54 and determines the trained model to which the TOF depiction image data 54 is to be input, on the basis of the judgment result.

Further, the PET image reconstructing circuitry 41d outputs the reconstructed PET image data 55, on the basis of a trained model that corresponds to the site subject to the scan performed at the time of acquiring the coincidence counting information from which the TOF depiction image data 54 is derived, the trained model being one of the plurality of trained models 53-1 to 53-n corresponding to the plurality of sites of the subject P.

The PET-CT apparatus 100 according to the third modification example has thus been explained. The PET-CT apparatus 100 according to the third modification example is able to shorten the time period required by the acquisition of the reconstructed PET image data, similarly to the PET-CT apparatus 100 according to the first embodiment and the PET-CT apparatuses 100 according to the other modification examples described above.

Fourth Modification Example

In the third modification example above, the example was explained in which the operator determines the trained model to which the TOF depiction image data 54 is to be input; however, the PET-CT apparatus 100 may be configured to automatically determine the trained model to which the TOF depiction image data 54 is to be input. Thus, this modification example will be explained as a fourth modification example. The following description of the fourth modification example will primarily explain differences from the third modification example.

The fourth modification example uses a trained model 56 configured to receive an input of the TOF depiction image data 54 and to output site information 57 indicating a site. The trained model 56 is stored in the storage circuitry 41a.

Figure 18:
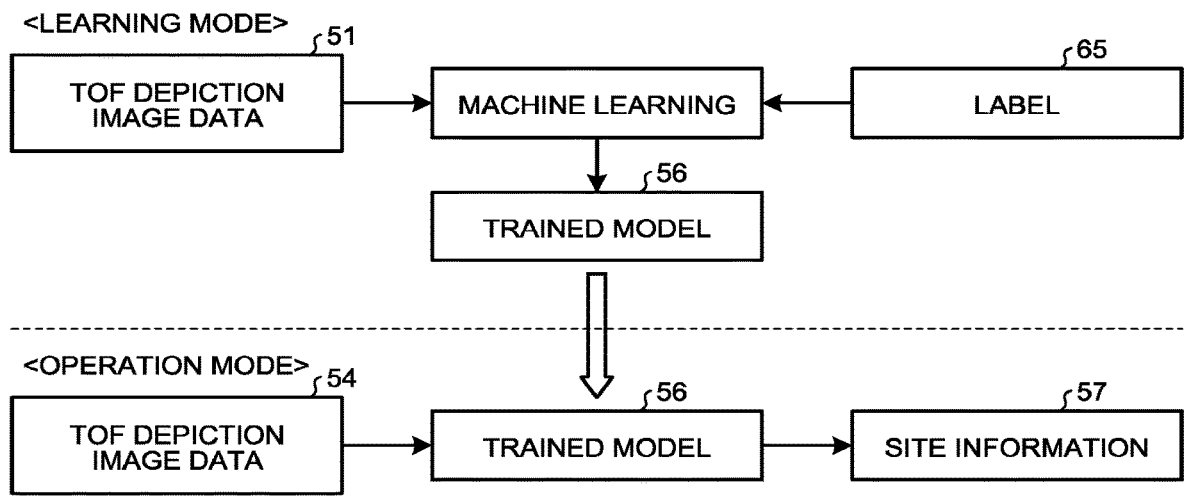
FIG. 18 is a chart for explaining examples of a process in a learning mode and a process in an operation mode according to a fourth modification example.

The trained model 56 will be explained with reference to FIG. 18. FIG. 18 is a chart for explaining examples of a process in a learning mode and a process in an operation mode according to the fourth modification example. As illustrated in FIG. 18, in the learning mode, the trained model generating device generates the trained model 56 by learning a relationship between the TOF depiction image data 51 and a label 65. The label 65 indicates a site subject to the scan performed at the time of acquiring the coincidence counting information from which the TOF depiction image data 51 is derived.

On the basis of the TOF depiction image data 54, the trained model 56 is configured to output the site information 57 indicating the site subject to the scan performed at the time of acquiring the coincidence counting information from which the TOF depiction image data 54 is derived.

For example, the trained model generating device is configured to perform machine learning by inputting, to a machine learning engine, a set made up of the TOF depiction image data 51 and the label 65 as learning-purpose data (training data).

As a result of the machine learning, the trained model generating device generates the trained model 56. Further, the trained model 56 generated by the trained model generating device is stored into the storage circuitry 41a.

Next, a process in the operation mode will be explained. When the switch button 45b is in the ON state, the PET image reconstructing circuitry 41d reads the TOF depiction image data 54 stored in the storage circuitry 41a. Further, as illustrated in FIG. 18 as a process in the operation mode, the PET image reconstructing circuitry 41d causes the trained model 56 to output the site information 57, by inputting the TOF depiction image data 54 to the trained model 56 stored in the storage circuitry 41a. After that, the PET image reconstructing circuitry 41d obtains the site information 57 output from the trained model 56. In other words, on the basis of the TOF depiction image data 54 and the trained model 56, the PET image reconstructing circuitry 41d outputs the site information 57. The PET image reconstructing circuitry 41d has thus derived the site information 57.

Further, from among the plurality of trained models 53-1 to 53-n, the PET image reconstructing circuitry 41d selects the trained model corresponding to the site indicated by the site information 57. After that, by inputting the TOF depiction image data 54 to the selected trained model, the PET image reconstructing circuitry 41d causes the trained model to output the reconstructed PET image data 55. Subsequently, the PET image reconstructing circuitry 41d obtains the reconstructed PET image data 55 output from the trained model. In other words, on the basis of the TOF depiction image data 54 and the selected trained model, the PET image reconstructing circuitry 41*d* outputs the reconstructed PET image data 55. The PET image reconstructing circuitry 41*d* has thus derived the reconstructed PET image data 55.

In other words, on the basis of the TOF depiction image data 54 and the trained model 56, the PET image reconstructing circuitry 41*d* is configured to derive the site information. Further, the PET image reconstructing circuitry 41*d* is configured to output the reconstructed PET image data 55, on the basis of the one of the plurality of trained models 53-1 to 53-*n* that corresponds to the site indicated by the derived site information.

The PET-CT apparatus 100 according to the fourth modification examples has thus been explained. The PET-CT apparatus 100 according to the fourth modification example is configured to automatically select the trained model from among the plurality of trained models 53-1 to 53-*n*. Accordingly, the PET-CT apparatus 100 according to the fourth modification example is able to reduce burdens on the operator. In addition, the PET-CT apparatus 100 according to the fourth modification example is able to shorten the time period required by the acquisition of the reconstructed PET image data, similarly to the PET-CT apparatus 100 according to the first embodiment and the PET-CT apparatuses 100 according to the other modification examples described above.

In the fourth modification example, the PET-CT apparatus 100 may be configured to automatically select a trained model from among the plurality of trained models 53-1 to 53-*n* by using a scanogram used for determining the position of the subject P or the like. For example, the position information of the PET gantry device 1 and the position information of the CT gantry device 2 are in correspondence with each other. Accordingly, the PET image reconstructing circuitry 41*d* detects a site from a scanogram in a position that matches the position of the TOF depiction image data 54. For example, the PET image reconstructing circuitry 41*d* may extract an anatomical feature point from the scanogram and detect the site on the basis of the anatomical feature point. After that, the PET image reconstructing circuitry 41*d* outputs the reconstructed PET image data 55, on the basis of one of the plurality of trained models 53-1 to 53-*n* that corresponds to the detected site.

The image data used for detecting the site does not necessarily have to be a scanogram used for position determining purposes and may be any image data in the position that matches the position of the TOF depiction image data 54.

Fifth Modification Example

In the third modification example, the example was explained in which the trained models respectively corresponding to the plurality of sites of the subject P are used; however, it is also acceptable to use trained models respectively corresponding to a plurality of types of drugs. Thus, this modification example will be explained as a fifth modification example. The following description of the fifth modification example will primarily explain differences from the first embodiment.

In the fifth modification example, for instance, a trained model is stored in the storage circuitry 41*a* for each of the types of drugs administered for the subject P. Each of the plurality of trained models is generated by learning a relationship between TOF depiction image data 51 based on coincidence counting information acquired by scanning the subject P for whom a corresponding type of drug was administered and PET image data 52 based on the coincidence counting information. In the fifth modification example, the plurality of trained models are stored in the storage circuitry 41*a*.

The display mode of the reconstructed PET image varies in accordance with the type of the drug. Accordingly, as a result using a trained model optimal for each of the drugs, it is expected that the learning may be easier, convergence in the learning mode may be achieved earlier, and the quality of the acquired reconstructed PET image may be better.

In the fifth modification example, in the operation mode, the operator determines which one of the plurality of trained models is to receive an input of the TOF depiction image data 54. In this manner, in the fifth modification example, the operator determines the drug corresponding to the TOF depiction image data 54 and determines the trained model to which the TOF depiction image data 54 is to be input, on the basis of the judgment result.

In other words, the PET image reconstructing circuitry 41*d* is configured to output the reconstructed PET image data 55, on the basis of the trained model corresponding to the type of the drug administered for the subject P in the scan performed at the time of acquiring the coincidence counting information from which the TOF depiction image data 54 is derived, the trained model being one of the plurality of trained models corresponding to the plurality of types of drugs.

The PET-CT apparatus 100 according to the fifth modification example has thus been explained. The PET-CT apparatus 100 according to the fifth modification example is able to shorten the time period required by the acquisition of the reconstructed PET image data, similarly to the PET-CT apparatus 100 according to the first embodiment and the PET-CT apparatuses 100 according to the other modification examples described above.

Sixth Modification Example

In the first embodiment, the example was explained in which the trained model generating device is configured to generate the trained model 53, by learning the TOF depiction image data 51 and the PET image data 52 that are kept in correspondence with each other; however, the trained model generating device may be configured to generate a trained model 53 by learning the TOF depiction image data 51, the PET image data 52, and an attenuation coefficient map that are kept in correspondence with one another. Thus, this modification example will be explained as a sixth modification example. The following description of the sixth modification example will primarily explain differences from the first embodiment.

Figure 19:
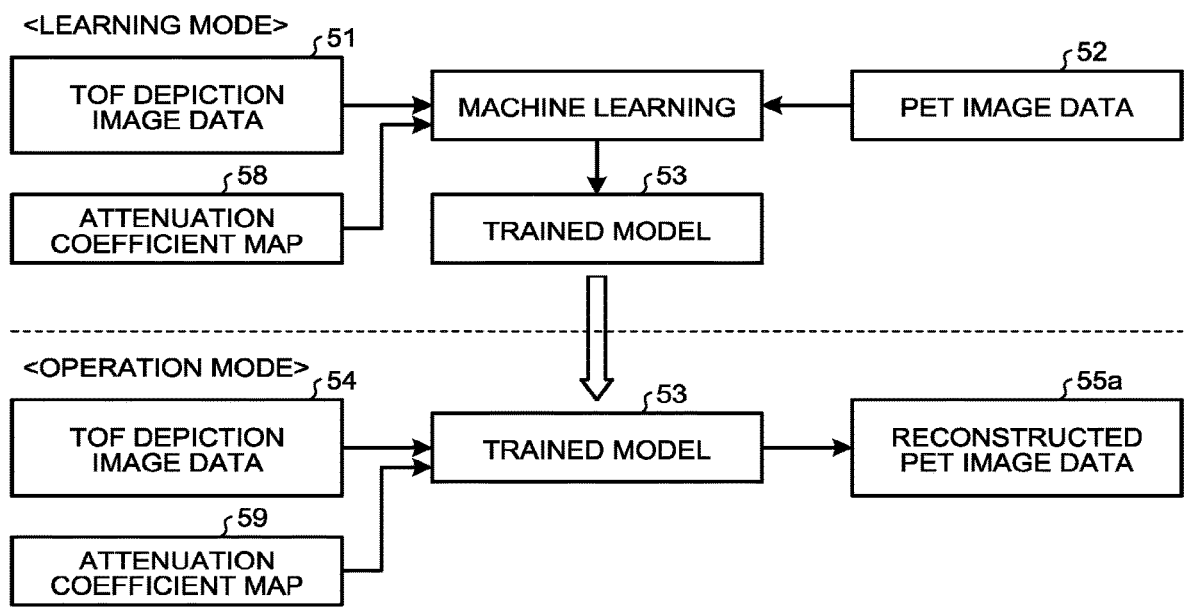
FIG. 19 is a chart for explaining examples of a process in a learning mode and a process in an operation mode according to a sixth modification example.

The trained model 53 according to the sixth modification example will be explained, with reference to FIG. 19. FIG. 19 is a chart for explaining examples of a process in the learning mode and a process in the operation mode according to the sixth modification example. As illustrated in FIG. 19, in the learning mode, the trained model generating device generates the trained model 53, by learning a relationship between the TOF depiction image data 51, the PET image data 52, and an attenuation coefficient map 58.

The attenuation coefficient map 58 is generated from CT image data acquired by performing a CT imaging process on the site subject to the scan performed at the time of acquiring the coincidence counting information from which the TOF depiction image data 51 is derived. For example, the X-ray CT image generating circuitry 42*c* is configured to generate the attenuation coefficient map 58. Alternatively, the attenuation coefficient map 58 may be generated from Magnetic Resonance (MR) image data acquired by performing an imaging process with a Magnetic Resonance Imaging (MRI) apparatus on the site subject to the scan performed at the time of acquiring the coincidence counting information from which the TOF depiction image data 51 is derived. The attenuation coefficient map 58 is obtained by mapping interaction probabilities between gamma rays of 511 kev detected by the PET gantry device 1 and the subject P. Accordingly, in the sixth modification example, the trained model 53 is generated while taking scattering and absorption of the gamma rays into account. It is therefore possible to generate the trained model 53 having an excellent level of precision.

In the sixth modification example, the trained model 53 is configured to output reconstructed PET image data 55a, on the basis of the TOF depiction image data 54 and an attenuation coefficient map 59. The attenuation coefficient map 59 is generated from CT image data acquired by performing a CT imaging process on the site subject to the scan performed at the time of acquiring the coincidence counting information from which the TOF depiction image data 54 is derived. For example, the X-ray CT image generating circuitry 42c generates the attenuation coefficient map 59. The reconstructed PET image data 55a is data having a higher level of precision than the reconstructed PET image data 55, because scattering, absorption, and the like of the gamma rays are taken into account.

In other words, the trained model generating device is configured to generate the trained model 53 according to the sixth modification example, by learning the TOF depiction image data 51, the PET image data 52, and the attenuation coefficient map 58 that are kept in correspondence with one another. Upon receipt of the input of the TOF depiction image data 54 and the attenuation coefficient map 59, the trained model 53 is configured to output the reconstructed PET image data 55a, which is image data corresponding to the PET image data 52.

For example, the trained model generating device is configured to perform machine learning by inputting, to a machine learning engine, a set made up of the TOF depiction image data 51, the PET image data 52, and the attenuation coefficient map 58, as learning-purpose data (training data).

As a result of this machine learning process, the trained model generating device generates the trained model 53. Further, the trained model 53 generated by the trained model generating device is stored into the storage circuitry 41a.

Next, a process in the operation mode will be explained. When the switch button 45b is in the ON state, the PET image reconstructing circuitry 41d reads the TOF depiction image data 54 stored in the storage circuitry 41a. Further, as illustrated in FIG. 19 as a process in the operation mode, the PET image reconstructing circuitry 41d causes the trained model 53 to output the reconstructed PET image data 55a, by inputting the TOF depiction image data 54 and the attenuation coefficient map 59 to the trained model 53 stored in the storage circuitry 41a. After that, the PET image reconstructing circuitry 41d obtains the reconstructed PET image data 55a output from the trained model 53. In other words, the PET image reconstructing circuitry 41d outputs the reconstructed PET image data 55a, on the basis of the TOF depiction image data 54, the attenuation coefficient map 59, and the trained model 53. The PET image reconstructing circuitry 41d has thus derived the reconstructed PET image data 55a.

In the learning mode, in place of the attenuation coefficient map 58, it is also acceptable to use CT image data acquired by performing a CT imaging process on the site subject to the scan performed at the time of acquiring the coincidence counting information from which the TOF depiction image data 51 is derived. Similarly, in the learning mode, in place of the attenuation coefficient map 58, it is also acceptable to use MR image data acquired by performing an imaging process with an MRI apparatus on the site subject to the scan performed at the time of acquiring the coincidence counting information from which the TOF depiction image data 51 is derived. In other words, in the learning mode, it is acceptable to use morphological image data such as the CT image data, the MR image data, or the like, in place of the attenuation coefficient map 58.

Further, in the operation mode, in place of the attenuation coefficient map 59, it is acceptable to use CT image data acquired by performing a CT imaging process on the site subject to the scan performed at the time of acquiring the coincidence counting information from which the TOF depiction image data 54 is derived. Similarly, in the operation mode, in place of the attenuation coefficient map 59, it is acceptable to use MR image data acquired by performing an imaging process with an MRI apparatus on the site subject to the scan performed at the time of acquiring the coincidence counting information from which the TOF depiction image data 54 is derived. In other words, in the operation mode, it is acceptable to use morphological image data such as the CT image data, the MR image data, or the like, in place of the attenuation coefficient map 59.

The PET-CT apparatus 100 according to the sixth modification example has thus been explained. The PET-CT apparatus 100 according to the sixth modification example is able to generate the trained model 53 having an excellent level of precision. Further, the PET-CT apparatus 100 according to the sixth modification example is able to shorten the time period required by the acquisition of the reconstructed PET image data, similarly to the PET-CT apparatus 100 according to the first embodiment and the PET-CT apparatuses 100 according to the other modification examples described above.

Second Embodiment

In the first embodiment and the various modification examples described above, the example was explained in which the PET-CT apparatus 100 is configured to derive the reconstructed PET image data by using the one or more trained models; however, the PET-CT apparatus 100 may derive reconstructed PET image data without using a trained model. Thus, this embodiment will be explained as a second embodiment. The following description of the second embodiment will primarily explain differences from the first embodiment. Further, in the description of the second embodiment, some of the constituent elements that are the same as those in the first embodiment will be referred to by using the same reference characters, and the explanations thereof may be omitted.

Figure 20:
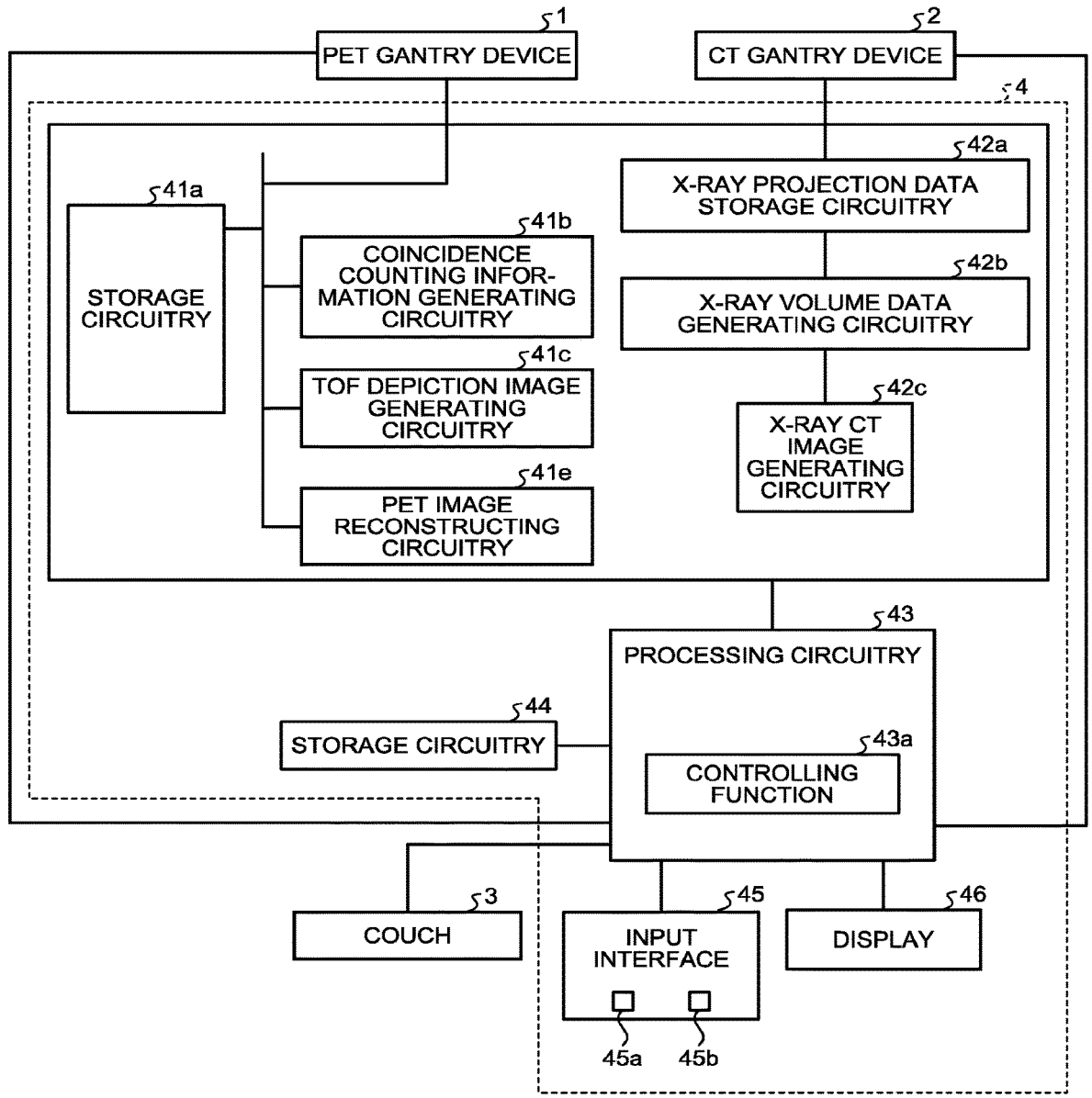
FIG. 20 is a diagram illustrating an exemplary configuration of a console device according to a second embodiment.

FIG. 20 is a diagram illustrating an exemplary configuration of the console device 4 according to the second embodiment. The console device 4 according to the second embodiment is different from the console device 4 according to the first embodiment for including PET image reconstructing circuitry 41e in place of the PET image reconstructing circuitry 41d according to the first embodiment. The PET image reconstructing circuitry 41e is realized by using a processor, for example.

Further, the second embodiment is different from the first embodiment in that the storage circuitry 41a does not have the trained model 53 stored therein.

The PET image reconstructing circuitry 41e is different from the PET image reconstructing circuitry 41d for being configured to derive the reconstructed PET image data 55 without using the trained model 53.

Figure 21:
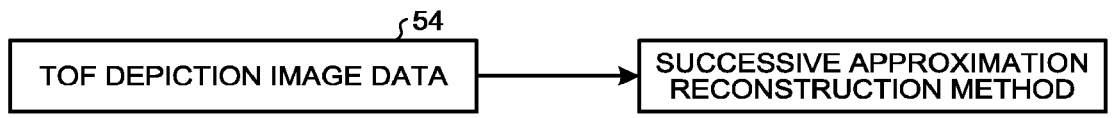
FIG. 21 is a drawing for explaining an example of a process performed by PET image reconstructing circuitry according to the second embodiment.

For example, the PET image reconstructing circuitry 41e is configured to read the TOF depiction image data 54 from the storage circuitry 41a. FIG. 21 is a drawing for explaining an example of a process performed by the PET image reconstructing circuitry 41e according to the second embodiment.

Generally speaking, in successive approximation reconstruction methods, blank image data is used as initial image data, so that final image data is obtained by statistically performing a successive approximation process.

In contrast, as illustrated in FIG. 21, the PET image reconstructing circuitry 41e according to the second embodiment is configured to reconstruct the reconstructed PET image data 55, by using the TOF depiction image data 54 as initial image data in the successive approximation reconstruction method. In other words, the PET image reconstructing circuitry 41e performs a successive approximation reconstructing process on the basis of the TOF depiction image data 54 so as to reconstruct the reconstructed PET image data 55 as final image data. In this situation, the difference between the initial image data and the final image data is smaller than the difference there is between the initial image data and the final image data when the initial image data is blank image data. For this reason, in the second embodiment, the number of times the successive processes are performed to obtain the final image data is smaller than the number of times the successive processes are performed when the initial image data is blank image data. Accordingly, the PET-CT apparatus 100 according to the second embodiment is able to shorten the time period required by the acquisition of the reconstructed PET image data 55. The PET image reconstructing circuitry 41e is an example of the reconstructing unit.

The PET-CT apparatus 100 according to the second embodiment has thus been explained. As explained above, the PET-CT apparatus 100 according to the second embodiment is able to shorten the time period required by the acquisition of the reconstructed PET image data 55.

In the embodiments and the modification examples described above, the examples were explained in which the PET-CT apparatus 100 is used as an example of the nuclear medicine diagnosis apparatus and the medical image diagnosis apparatus; however, another nuclear medicine diagnosis apparatus or another medical image diagnosis apparatus such as a PET apparatus or a PET-MR apparatus may perform the same processes as those performed by the PET-CT apparatus 100.

Third Embodiment

In the first and the second embodiments and the various modification examples described above, the examples were explained in which the PET-CT apparatus 100 performs the various types of processes; however, a medical image processing apparatus may perform the same processes. Thus, this embodiment will be explained as a third embodiment.

Figure 22:
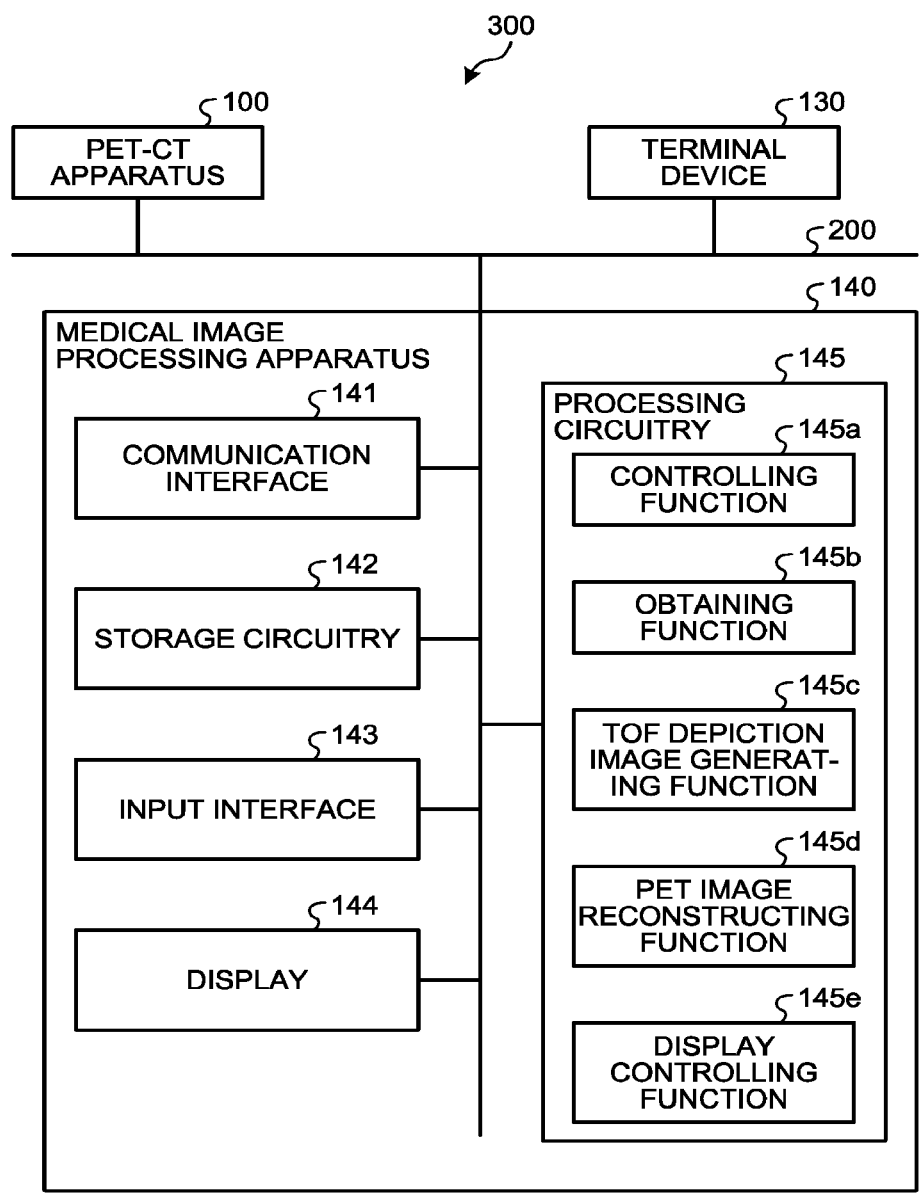
FIG. 22 is a diagram illustrating an exemplary configuration of a medical image processing system according to a third embodiment.

FIG. 22 is a diagram illustrating an exemplary configuration of a medical image processing system 300 according to the third embodiment. As illustrated in FIG. 22, the medical image processing system 300 according to the present embodiment includes the PET-CT apparatus 100, a terminal device 130, and a medical image processing apparatus 140. In this situation, the apparatuses and the device are communicably connected to one another via a network 200.

The PET-CT apparatus 100 is configured to transmit the time-series list of the coincidence counting information, the attenuation coefficient map 59, and various types of trained models (e.g., the trained models 53 and 53-1 to 53-n) to the medical image processing apparatus 140. Further, the PET-CT apparatus 100 is configured to transmit the TOF depiction image data 54, the reconstructed PET image data 55 and 55a, and the like to the terminal device 130.

The terminal device 130 is a device for enabling medical doctors and medical technologists working at the hospital to view medical images. For example, the terminal device 130 is realized by using a Personal Computer (PC), a tablet PC, a Personal Digital Assistant (PDA), a mobile phone, or the like that is operated by the medical doctors and the medical technologists working at the hospital. For example, the terminal device 130 is configured to cause a display monitor thereof to display the TOF depiction image represented by the TOF depiction image data 54 and reconstructed PET images represented by the reconstructed PET image data 55 and 55a received from either the PET-CT apparatus 100 or the medical image processing apparatus 140.

The medical image processing apparatus 140 is configured to obtain, from the PET-CT apparatus 100, the time-series list of the coincidence counting information, the attenuation coefficient map 59, and the various types of trained models, and to store the time-series list of the coincidence counting information, the attenuation coefficient map 59, and the various types of trained models into storage circuitry 142. Further, the medical image processing apparatus 140 is configured to perform the same processes as those performed by the console device 4 above, by using the time-series list of the coincidence counting information, the attenuation coefficient map 59, and the various types of trained models. For example, the medical image processing apparatus 140 is realized by using a computer device such as a server, a workstation, a personal computer, a tablet terminal, or the like.

As illustrated in FIG. 22, the medical image processing apparatus 140 includes a communication interface 141, the storage circuitry 142, an input interface 143, a display 144, and processing circuitry 145.

The communication interface 141 is connected to the processing circuitry 145 and is configured to control communication performed between the medical image processing apparatus 140 and various types of apparatuses and devices. More specifically, the communication interface 141 is connected to the various types of apparatuses and devices (e.g., the PET-CT apparatus 100 and the terminal device 130) via the network 200 and is configured to receive various types of data and information from the apparatuses and devices and to output the received data and information to the processing circuitry 145. For example, the communication interface 141 is realized by using a network card, a network adaptor, a Network Interface Controller (NIC), or the like.

The storage circuitry 142 is connected to the processing circuitry 145 and is configured to store therein various types of data and information. For example, the storage circuitry 142 has stored therein the time-series list of the coincidence counting information, the attenuation coefficient map 59, the various types of trained models, and the like transmitted thereto from the PET-CT apparatus 100. Further, the storage circuitry 142 has stored therein various types of programs for realizing various types of functions when being read and executed by the processing circuitry 145. For example, the storage circuitry 142 is realized by using a semiconductor memory element such as a flash memory, or a hard disk, an optical disk, or the like. The storage circuitry 142 is an example of a storage unit.

The input interface 143 is connected to the processing circuitry 145 and is configured to receive operations to input various types of instructions and information from the operator. More specifically, the input interface 143 is configured to convert the input operations received from the operator into electrical signals and to output the electrical signals to the processing circuitry 145. For example, the input interface 143 is realized by using a trackball, a switch button, a mouse, a keyboard, a touchpad on which an input operation is performed by touching an operation surface thereof, a touch screen in which a display screen and a touchpad are integrally formed, a contactless input circuit using an optical sensor, an audio input circuit, and/or the like. In the present disclosure, the input interface 143 does not necessarily have to include physical operation component parts such as a mouse, a keyboard, and/or the like. Possible examples of the input interface 143 include electrical signal processing circuitry configured to receive an electrical signal corresponding to an input operation from an external input device provided separately from the apparatus and to output the received electrical signal to the processing circuitry 145. The input interface 143 is provided with two switch buttons (not illustrated) having the same functions as those of the switch button 45a and the switch button 45b described above.

The display 144 is connected to the processing circuitry 145 and is configured to display various types of information and images. More specifically, the display 144 is configured to convert data of the information and images sent thereto from the processing circuitry 145 into display-purpose electrical signals and to output the display-purpose electrical signals. For example, the display 144 is realized by using a liquid crystal monitor, a Cathode Ray Tube (CRT) monitor, a touch panel, or the like. The display 144 is an example of a display unit.

The processing circuitry 145 is configured to control operations of the medical image processing apparatus 140 in accordance with input operations received from the operator via the input interface 143. For example, the processing circuitry 145 is realized by using a processor.

As illustrated in FIG. 22, the processing circuitry 145 of the medical image processing apparatus 140 is configured to execute a controlling function 145a, an obtaining function 145b, a TOF depiction image generating function 145c, a PET image reconstructing function 145d, and a display controlling function 145e. The obtaining function 145b is an example of an obtaining unit. The PET image reconstructing function 145d is an example of a processing unit and the reconstructing unit.

The controlling function 145a is configured to control the interfaces 141 and 143, the storage circuitry 142, the display 144, and the functions 145b to 145e of the medical image processing apparatus 140 so as to perform processes corresponding to various types of requests input via the input interface 143. For example, the controlling function 145a is configured to control transmission and reception of various types of data and various types of information performed via the communication interface 141, as well as storing of data and information into the storage circuitry 142, and the like.

For example, the controlling function 145a is configured to store the time-series list of the coincidence counting information, the attenuation coefficient map 59, and the various types of trained models transmitted thereto from the PET-CT apparatus 100, into the storage circuitry 142.

The obtaining function 145b is configured to obtain various types of data. For example, the obtaining function 145b is configured to obtain the time-series list of the coincidence counting information stored in the storage circuitry 142. The obtained time-series list of the coincidence counting information is used when the TOF depiction image generating function 145c generates the TOF depiction image data 54.

Further, the obtaining function 145b is configured to obtain the TOF depiction image data 54, the attenuation coefficient map 59, and the various types of trained models stored in the storage circuitry 142. The TOF depiction image data 54, the attenuation coefficient map 59, and the various types of trained models having been obtained are used when the PET image reconstructing function 145d derives the reconstructed PET image data 55 and 55a.

The TOF depiction image generating function 145c has the same functions as those of the TOF depiction image generating circuitry 41c. The TOF depiction image generating function 145c is configured to generate the TOF depiction image data 54, by using the time-series list of the coincidence counting information obtained by the obtaining function 145b. Further, the TOF depiction image generating function 145c is configured to store the TOF depiction image data 54 into the storage circuitry 142.

The PET image reconstructing function 145d has the same functions as those of the PET image reconstructing circuitries 41d and 41e. For example, the PET image reconstructing function 145d is configured to derive the reconstructed PET image data 55 and 55a by using the TOF depiction image data 54, the attenuation coefficient map 59, and the various types of trained models obtained by the obtaining function, similarly to the PET image reconstructing circuitries 41d and 41e.

The display controlling function 145e has the same functions as those of the controlling function 43a. For example, the display controlling function 145e is configured to cause the display 144 to display the TOF depiction image represented by the TOF depiction image data 54 and the reconstructed PET images represented by the reconstructed PET image data 55 and 55a.

The medical image processing apparatus 140 according to the third embodiment has thus been explained. The medical image processing apparatus 140 according to the third embodiment is able to shorten the time period required by the acquisition of the reconstructed PET image data, similarly to the PET-CT apparatuses 100 according to the embodiments described above and the PET-CT apparatuses 100 according to the modification examples described above.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the storage circuitry 142. Further, instead of saving the programs in the storage circuitry 142, it is also acceptable to directly incorporate the programs into the circuits of the processors. In that situation, the processors realize the functions by reading and executing the programs incorporated in the circuits thereof. Further, each of the processors of the present embodiments does not necessarily have to be structured as a single circuit. It is also acceptable to structure one processor by combining together a plurality of independent circuits so as to realize the functions thereof.

In the present example, a processing program executed by the processors is provided as being incorporated, in advance, in a Read Only Memory (ROM), a storage unit, or the like. The processing program may be provided as being stored in a computer-readable storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by these devices. Further, the processing program may be stored in a computer connected to a network such as the Internet so as to be provided or distributed as being downloaded via the network. For example, the processing program is structured with modules including the above functional units. In the actual hardware, as a result of a CPU reading and executing the program from a storage medium such as a ROM, the modules are loaded into a main storage device and generated in the main storage device.

The constituent elements of the apparatuses and devices in the drawings of the above embodiments are based on functional concepts. Thus, it is not necessary to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions performed by the apparatuses and devices may be realized by a CPU and a program analyzed and executed by the CPU or may be realized as hardware using wired logic.

According to at least one aspect of the embodiments described above, it is possible to shorten the time period required by the acquisition of the reconstructed PET image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to:
obtain Time-of-Flight (TOF) depiction image data generated on a basis of an annihilation point of a gamma ray, the TOF depiction image data representing a TOF depiction image in which annihilation point indicating a position of occurrence of annihilation event is depicted as a point or a line; and
output reconstructed Positron Emission computed Tomography (PET) image data on a basis of the TOF depiction image data and a trained model that outputs the reconstructed PET image data on a basis of an input of the TOF depiction image data,
wherein the processing circuitry outputs the reconstructed PET image data, on a basis of the trained model corresponding to a type of drug administered for a subject in a scan at a time of acquiring coincidence counting information from which the obtained TOF depiction image data is derived, the trained model being one of a plurality of trained models corresponding to a plurality of types of drugs.

2. The medical image processing apparatus according to claim 1, wherein the processing circuitry outputs the reconstructed PET image data, on the basis of the trained model generated by learning a plurality of pieces of TOF depiction image data having a plurality of mutually-different noise levels.

3. The medical image processing apparatus according to claim 1, wherein the processing circuitry obtains the TOF depiction image data based on coincidence counting information acquired with respect to each of sections of a subject.

4. The medical image processing apparatus according to claim 1, wherein the processing circuitry obtains the TOF depiction image data based on coincidence counting information acquired while a subject is being moved relative to a PET gantry device.

5. The medical image processing apparatus according to claim 1, wherein the processing circuitry outputs the reconstructed PET image data, on a basis of the trained model corresponding to a site subject to a scan performed at a time of acquiring coincidence counting information from which the obtained TOF depiction image data is derived, the trained model being one of a plurality of trained models corresponding to a plurality of sites of a subject.

6. The medical image processing apparatus according to claim 5, wherein
the processing circuitry derives site information indicating a site, on a basis of the obtained TOF depiction image data and another trained model that outputs the site information on a basis of an input of the TOF depiction image data, and
the processing circuitry outputs the reconstructed PET image data, on a basis of one of the plurality of trained models that corresponds to the site indicated by the derived site information.

7. The medical image processing apparatus according to claim 5, wherein
the processing circuitry detects a site from image data in a position that matches a position of the obtained TOF depiction image data, and
the processing circuitry outputs the reconstructed PET image data on a basis of one of the plurality of trained models that corresponds to the detected site.

8. The medical image processing apparatus according to claim 1, wherein the processing circuitry outputs the reconstructed PET image data, on a basis of the TOF depiction image data, an attenuation coefficient map, and the trained model that outputs the reconstructed PET image data on a basis of inputs of the TOF depiction image data and the attenuation coefficient map.

9. The medical image processing apparatus according to claim 1, wherein the processing circuitry outputs the reconstructed PET image data, on a basis of the TOF depiction image data, morphological image data, and the trained model that outputs the reconstructed PET image data on a basis of inputs of the TOF depiction image data and the morphological image data.

10. The medical image processing apparatus according to claim 1, comprising an interface capable of selecting whether the processing circuitry is caused to reconstruct the reconstructed PET image data by implementing a successive approximation reconstruction method or the processing circuitry is caused to derive the reconstructed PET image data by using the TOF depiction image data.

11. A nuclear medicine diagnosis apparatus comprising:
processing circuitry configured to:
acquire Time-of-Flight (TOF) depiction image data generated on a basis of an annihilation point of a gamma ray, the TOF depiction image data representing a TOF depiction image in which annihilation point indicating a position of occurrence of annihilation event is depicted as a point or a line; and
output reconstructed Positron Emission computed Tomography (PET) image data on a basis of the TOF depiction image data and a trained model that outputs the reconstructed PET image data on a basis of an input of the TOF depiction image data,
wherein the processing circuitry outputs the reconstructed PET image data, on a basis of the trained model corresponding to a type of drug administered for a subject in a scan at a time of acquiring coincidence counting information from which the obtained TOF depiction image data is derived, the trained model being one of a plurality of trained models corresponding to a plurality of types of drugs.

\* \* \* \* \*